(12) United States Patent
Babcock

(10) Patent No.: US 12,263,480 B2
(45) Date of Patent: Apr. 1, 2025

(54) DIAGNOSTIC DEVICE WITH INTEGRATED SAMPLER AND HOLDER

(71) Applicant: Brian David Babcock, Columbia, TN (US)

(72) Inventor: Brian David Babcock, Columbia, TN (US)

( * ) Notice: Subject to any disclaimer, the term of this patent is extended or adjusted under 35 U.S.C. 154(b) by 727 days.

(21) Appl. No.: 17/465,078

(22) Filed: Sep. 2, 2021

(65) Prior Publication Data

US 2022/0097044 A1 Mar. 31, 2022

Related U.S. Application Data

(60) Provisional application No. 63/074,553, filed on Sep. 4, 2020.

(51) Int. Cl.
| | | |
|---|---|---|
| *B01L 3/00* | (2006.01) | |
| *G01N 33/02* | (2006.01) | |
| *G01N 33/18* | (2006.01) | |
| *G01N 33/24* | (2006.01) | |
| *G01N 33/52* | (2006.01) | |

(52) U.S. Cl.
CPC ......... *B01L 3/50273* (2013.01); *B01L 3/5023* (2013.01); *B01L 3/565* (2013.01); *G01N 33/02* (2013.01); *G01N 33/18* (2013.01); *G01N 33/24* (2013.01); *G01N 33/521* (2013.01); *B01L 2200/0689* (2013.01); *B01L 2300/042* (2013.01); *B01L 2300/161* (2013.01)

(58) Field of Classification Search
CPC .... B01L 3/50273; B01L 3/5023; B01L 3/565; B01L 2200/0689; B01L 2300/042; B01L 2300/161; B01L 3/502746; B01L 2200/027; B01L 2200/0621; B01L 2300/0663; B01L 2400/088; G01N 33/02; G01N 33/18; G01N 33/24; G01N 33/521; G01N 33/54388
See application file for complete search history.

(56) References Cited

U.S. PATENT DOCUMENTS 9,522,397 B2 * 12/2016 Khattak ............ B01L 3/502738

* cited by examiner

*Primary Examiner* — Dennis White

(57) ABSTRACT

An analytical and/or diagnostic device that includes a compartment for reagents stored within the device and uses surface energy gradient coatings to move liquid through fluid passages. The device can include a sampler for collecting a sample, a reaction region for reagents to react with the sample, and a detection region to detect any species of interest present in the sample.

20 Claims, 13 Drawing Sheets

DIAGNOSTIC DEVICE WITH INTEGRATED SAMPLER AND HOLDER

CROSS-REFERENCES TO RELATED APPLICATIONS

This application is a nonprovisonal application that claims priority and benefit of provisional application 63/074,553, filed Sep. 4, 2020, the contents of which are herein incorporated by reference in their entirety.

STATEMENT REGARDING FEDERALLY SPONSORED RESEARCH OR DEVELOPMENT

Not Applicable.

PARTIES TO A JOINT RESEARCH AGREEMENT

Not Applicable

FIELD OF THE INVENTION

The present invention relates to microfluidic analytical products using surface energy gradient coatings to control fluid flow within the product.

BACKGROUND OF THE INVENTION

The use of microfluidic technology is suitable for a number of analytical chemical and biochemical operations, particularly in diagnostic devices. Diagnostic devices often perform chemical and biochemical reactions that range from the simple to the relatively complex. Considerable interest has been focused on microfluidic techniques, which typically involve small sample volumes and low reagent consumption. The small size of these microfluidic devices can allow for the performance of reactions at substantially greater rates, and with substantially less reagent volume. Such devices may be used to carry out numerous parallel processes, can be used across a range of fluid properties, and are compatible with movement of biological moieties that may vary by orders of magnitude in size and physical characteristics.

Microfluidic analytical devices may employ a body structure or substrate that has at least one microscale channel disposed within it. Examples of such systems range from simple tubular capillary systems, e.g., fused silica capillaries, to more complex planar devices that can have from one to several intersecting channels disposed therein, i.e., between at least two planar substrate layers. Microfluidic systems generally have a broad range of uses including separation and characterization of macromolecular species, e.g., proteins and nucleic acids, see e.g., U.S. Pat. No. 5,699,157, screening assay platforms, e.g., drug screening, diagnostics, etc.

The above-described microfluidic devices, however, pose certain technical challenges that must be overcome. For example, fluid flow characteristics within the small flow channels of a microfluidic device may differ from the flow characteristics of fluids in larger devices, since surface effects tend to predominate, and regions of bulk flow become proportionately smaller. Several techniques have been developed in order to achieve fluid flow control in microfluidic devices. One technique involves the generation of electric fields to manipulate buffered, conductive fluids around networks of channels through electrophoretic or electroosmotic forces. See, e.g., Culbertson et al. (2000), "Electroosmotically induced hydraulic pumping on microchips: differential ion transport," Anal. Chem. 72:2285-2291. Another technique, as described in Anderson et al. (2000), "A miniature integrated device for automated multistep genetic assays," Nucleic Acids Res. 28:E60, describes fluidic control by coupling the device to an external system of solenoid valves and pressure sources. However, these fluid control mechanisms greatly increase the complexity, cost, and manufacturability of such highly integrated designs.

Typically, microfluidic diagnostic devices employ fluid or material direction systems to transport fluids or other materials through and among the channels and chambers of the device in order to perform the combinations, separations or other operations in carrying out a given analysis. Other devices require an operator or laboratory technician to perform several steps such as reagent addition or sample extraction outside the device and then add a solution to the device. For many applications (e.g., sensors, diagnostics, and other microfluidic devices), the ability to precisely control the wetting, mixing, and/or flow of a liquid within the passages of the device would provide a great benefit. Thus, it would be desirable to have additional methods and materials that can provide such control, particularly without requiring any additional steps from an operator or technician after the sample to be analyzed is loaded into the device.

Wetting behavior of a liquid on a substrate surface is typically a function of the surface energy of the substrate surface and the surface tension of the liquid. At the liquid-substrate surface interface, if the molecules of the liquid have a stronger attraction to the molecules of the substrate surface than to each other (the adhesive forces are stronger than the cohesive forces), then wetting of the substrate surface generally occurs. Alternatively, if the molecules of the liquid are more strongly attracted to each other than to the molecules of the substrate surface (the cohesive forces are stronger than the adhesive forces), then the liquid generally beads-up and does not wet the surface of the substrate. One way to quantify surface wetting characteristics of a liquid on a surface of a substrate is to measure the contact angle of a drop of liquid placed on that surface. The contact angle is the angle formed by the solid/liquid interface and the liquid/vapor interface measured from the side of the liquid. Typically, a decrease in the contact angle between the liquid and the surface correlates with an increase in wetting.

Surface energy gradients are useful for transporting small fluid volumes in analytical or medical devices while reducing or eliminating external forces. A microfluidic product using these gradients needs less energy to operate and could be shrunk to smaller sizes to be less invasive. In addition, the use of surface energy gradients to control fluid flow, including stopping and initiating flow within the microfluidic product can reduce or eliminate the need for expensive pumps and controllers in the overall system, greatly reducing the cost of current systems. For diagnostic devices utilizing such gradient coatings to control the flow of reagent addition, sample mixing, sample extraction, and other features, the device could include all the required extraction, reagent, and detection species on-board and could perform one or more analyses without requiring any effort from an operator or technician after the sample is loaded into the device.

A microfluidic product utilizing these gradients could be produced at similar or lower cost than current products and would also reduce the cost and complexity of external hardware and also the size of any individual components (analytical slides, cartridges, etc.). In addition, because the gradients can be created with small, precise dimensions, a component utilizing one or more surface energy gradients can also reduce the amount of solution used in the system. Because of the improved fluid transport properties due the surface energy gradients, the amount of solution loss due to hold-up in channels, wells, passages, etc. would also be greatly reduced.

New devices using surface energy gradients would have a great benefit. The invention has particular value for product applications that use high-volume, disposable parts.

SUMMARY OF THE INVENTION

An embodiment of the invention is an analytical or diagnostic product that uses surface energy gradient coatings to control fluid flow within channels and other fluid passages. The composition of the gradients as well as the degree of the gradient can be adjusted to control different aspects of fluid flow, including fluid velocity and stopping and starting fluid flow. The diagnostic product can use one or more gradient compositions in a plurality of channels to provide for different flow rates within different channels on a single product. The diagnostic product can comprise on-board reagents and detection agents disposed within channels, wells, enclosures, and other regions of the product. Surface energy gradient coatings can be used to control the flow of the on-board reagent and detection agents to provide sample extraction and mixing, binding of species to be detected, detection of species, and other process steps. The gradient coatings can be used to control all the liquid flows in the product to ensure that all extraction steps, reaction and bonding steps, and detection steps are provided sufficient time to reach a targeted completion and are performed in the correct order.

The analytical product can be a diagnostic product that is used to detect a sample for the presence of allergens, including allergen species found in peanuts, nuts, shellfish, fish, eggs, dairy products, wheat, soybeans, corn, and other foods. The diagnostic product can detect a plurality of allergens species that may be present in a single sample. The diagnostic product can be used to detect specific proteins present in foods to determine if a food sample contains any allergen species of concern.

In other embodiments, the analytical product may be used to carry out multiple assay tests, including panels of assays for analytes or activities associated with a specific biochemical system, biochemical pathway, tissue, organism, cell type, organelle, disease state, class of receptors, class of enzymes, class of pathogen, environmental sample, food sample, etc. Other embodiments can comprise panels that include drugs of abuse, therapeutic drugs, auto-antibodies (e.g., one or more antibodies directed against the Sm, RNP, SS-A, SS-B Jo-1, and Scl-70 antigens), allergen specific antibodies, tumor markers, cardiac markers (e.g., one or more of Troponin T, Troponin I, myoglobin, CKMB, etc.), markers associated with hemostasis (e.g., one or more of Fibrin monomer, D-dimer, thrombin-antithrombin complex, prothrombin fragments 1 & 2, anti-Factor Xa, etc.), markers of fertility (e.g., one or more of Estradiol, progesterone, follicle stimulating hormone (FSH), luetenizing hormone (LH), prolactin, beta-hCG; testosterone, etc.), markers of congestive heart failure, markers of thyroid disorders, and markers of prostrate cancer (e.g., one or more of total PSA, free PSA, complexed PSA, prostatic acid phosphatase, creatine kinase, etc.), pathogens and/or associated with upper respiratory infection and other respiratory conditions (e.g., influenza A, influenza B, Respiratory Syncytial Virus, Streptococci species, coronaviruses), pathogens found in food and water (e.g., *Salmonella, Listeria*, cryptosporidia, *Campylobacter, E. Coli* 0157, etc.), sexually transmitted diseases (e.g., HIV, syphilis, herpes, gonorrhea, HPV, etc.), blood borne pathogens and potential bioterrorism agents (e.g., pathogens and toxins in the CDC lists of Select A, B and C agents such as *B. anthracis, Y. pestis*, small pox, *F. tularensis*, ricin, botulinum toxins, staph enterotoxins, etc.).

One embodiment is a microfluidic product that utilizes surface energy gradients for fluid control comprising a plurality of fluid passages wherein the fluid passages each comprise a top and a bottom surface wherein at least one fluid passage comprises a gradient surface energy region beginning at a proximal location on a surface of the fluid passage and ending at a distal location on a surface of the fluid passage. The product can include uniform regions and surface gradient regions in the same passage. Coating compositions and product dimensions can be selected to provide control over different flow properties including fluid velocity, reduction and acceleration of fluid flow, and starting and stopping fluid flow.

In an embodiment, the microfluidic product comprises one or more fluid passages wherein a first fluid passage comprises a top and a bottom surface wherein the first fluid passage comprises a coating configured to control liquid flow wherein the coating comprises a gradient surface energy coating from a proximal location to a distal location on a surface of the fluid passage. In an embodiment, the microfluidic product comprises a plurality of fluid passages wherein the plurality of fluid passages comprise a first fluid passage and a second fluid passage, each with a top and a bottom surface, wherein both the first fluid passage and the second fluid passage comprise a coating configured to control liquid flow wherein the coating comprises a gradient surface energy coating from a proximal location to a distal location on a surface of the fluid passage. In an embodiment, the contact angle formed with water and a surface at a proximal location of the surface energy gradient in the first fluid passage is different from the contact angle formed with water and a surface at a proximal location of the surface energy gradient in the second fluid passage. In an embodiment, the contact angle formed with water and a surface at a distal location of the surface energy gradient in the first fluid passage is different from the contact angle formed with water and a surface at a distal location of the surface energy gradient in the second fluid passage. In an embodiment, the first fluid passage and the second fluid passage are in fluid communication with each other. In an embodiment, the microfluidic product further comprises a fluid passage that is not coated. In embodiments, the fluid passages comprise rectangular or non-rectangular channels. In embodiments, the fluid passages comprise circular channels. In embodiments, the fluid passages comprise non-circular channels. In embodiments, the coating configured to control liquid flow is on the bottom surface of the fluid passage. In embodiments, the coating configured to control liquid flow is on the top surface of the fluid passages. In embodiments, the top and bottom surfaces of the fluid passages are coated with different coating compositions.

U.S. Pat. No. 7,790,265 discloses surface energy gradients comprised of mixed monolayer films and discloses different methods for producing such gradients. The entire content of U.S. Pat. No. 7,790,265 patent is incorporated by reference into this application.

The surface can be a wide variety of materials including metals, glasses, plastics, ceramics, etc. In addition, the surface can be a base substrate of either rigid or flexible material that contains a base coating. The base coating can be metallic, ceramic, or polymeric.

In an embodiment the surface is a nonwoven material or a film or other flexible material. In an embodiment, the nonwoven material or film comprises a metallic coating such as aluminum, nickel, gold, silver, copper, or other materials. Multiple methods can be used to apply metallic coatings to different film or nonwoven surfaces.

One embodiment of the invention is an analytical device wherein the surface energy gradient resides on a flexible film and the film is attached to or placed in contact with the top or bottom surface of a plastic material containing channels and/or wells intended for fluid transport and/or analysis. The film can be used to seal the top or bottom of the channel (or both the top and bottom) to form a device with channels containing a surface energy gradient on at least one surface. The width of the gradient coating can be different from the width of the channel. In some instances, it may be desirable to keep the drop confined to the gradient region without touching the plastic, non-gradient walls of the channel. In other instances, it may be desirable from a manufacturing standpoint to manufacture the surface energy gradients in the film with a wider width than the width of the channels and overlay and seal the film over the channels.

Additional embodiments of products and their design features that utilize surface energy gradient coatings are disclosed in U.S. Pat. No. 9,968,930 "Microfluidic Products with Controlled Fluid Flow", which is herein incorporated by reference.

An embodiment includes an analytical device that comprises
1) A sample region comprising an opening and a first cavity within the device configured to receive a sample and closure means for covering the opening,
2) A second cavity comprising an extraction solvent or extraction reagent within the device,
3) An extraction region configured to receive at least a portion of the sample from the sample region and at least a portion of the extraction solvent,
4) A reaction region comprising one or more reaction reagents wherein the reaction region is located downstream of the extraction region and is configured to receive liquid flowing from the extraction region,
5) A first fluid passage connecting the extraction region to the reaction region wherein the first fluid passage comprises a first surface energy gradient coating,
6) A detection region comprising one or more detection agents wherein the detection region is located downstream of the reaction region and is configured to receive liquid flowing from the reaction region, and
7) A second fluid passage connecting the reaction region to the detection region wherein the second fluid passage comprises a second surface energy gradient coating, An embodiment also includes a method of analyzing a sample for the presence of species of concern comprising the following steps:
1) Introducing a sample into the sample region of an analytical device and using closure means to enclose the sample within the device,
2) Contacting the sample with an extraction solvent wherein the extraction solvent extracts species of concern from the sample for a first target contact time
3) After the first target contact time has been reached, transferring the solution produced from the extraction solvent and the species of concern from the sample region through a first fluid passage comprising a first surface energy gradient coating to a separate reaction region comprising one or more reaction reagents,
4) Contacting the solution containing the species of concern with the one or more reaction reagents in the reaction region for a second target contact time to produce a solution comprising reaction products,
5) After the second contact time has been reached, transferring the solution comprising the reaction products from the reaction region through a second fluid passage comprising a second surface energy gradient coating to a detection region comprising one or more detection agents,
6) Contacting the solution comprising the reaction products with one or more detection agents in the detection region for a third target contact time to produce a detection response.

An embodiment of the disclosure can be an analytical device comprising
1) A first sealed compartment comprising an extraction solvent or extraction reagent within the device wherein the first compartment comprises a seal over an opening,
2) A second compartment comprising an opening, wherein the opening of the second compartment is aligned with the opening of the first compartment,
3) A reaction region comprising one or more reaction reagents wherein at least a portion of the reaction region is located below at least a portion of the first or second compartment and is configured to receive liquid flowing from the first or second compartment.
4) A first fluid passage connecting the first or second compartment to the reaction region wherein the first fluid passage comprises a first surface energy gradient coating,
5) A detection region comprising one or more detection agents wherein the detection region is located downstream of the reaction region and is configured to receive liquid flowing from the reaction region.
6) A third compartment having an opening wherein at least a portion of the third compartment is located above the reaction region, and
7) wherein the openings of the first, second, and third compartments are configured to receive at least a portion of a sampler.

DETAILED DESCRIPTION OF THE INVENTION

Figure 1:
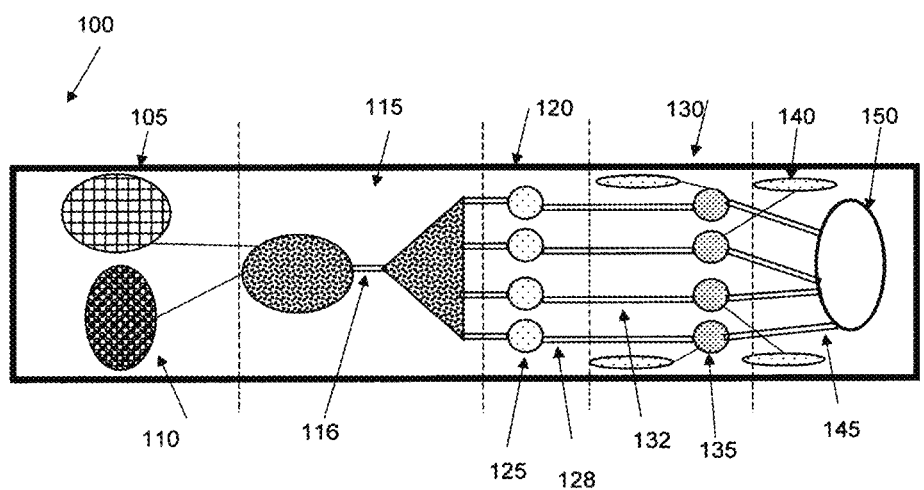
FIG. 1 is a drawing showing an embodiment of the disclosure.

An embodiment of the disclosure is a test device that can analyze a food sample for the presence of allergens. The device is useful for those who know they or their children have a severe allergy to certain foods (peanuts, tree nuts, soybeans, shellfish, eggs, fish, dairy, soybeans, etc.). It could also be used at manufacturing facilities, schools, hospital, restaurants, or other businesses to determine if a food has been contaminated with allergens of concern. In many cases, people with allergies of concern are allergic to several items or may have more severe reactions to specific proteins. The device could test for a panel of allergens using a single sample.

The device can have all the reagents, solvents, detection agents, etc. stored on board. The user or technician would only need to add a sample of the food to the sample collection area and the device will perform the remaining functional steps without further input from the user—extraction from the sample, mixing, flow to the reaction and detection areas. The device can use detection methods' that are visible to the naked eye. The device of the disclosure could also use detection methods that rely on camera capabilities on a smartphone, tablet, or other electronic device to provide good detection measurements as well. In some embodiments, the product may use a control measurement to make sure sample mixing, flow control, reaction, and/or detection functions are working correctly.

The analytical product can be a diagnostic product that is used to detect a sample for the presence of allergens, including allergen species found in peanuts, tree nuts, shellfish, fish, eggs, dairy products, wheat, soybeans, corn, and other foods. The diagnostic product can detect a plurality of allergens species that may be present in a single sample. The diagnostic product can be used to detect specific proteins present in foods to determine if a food sample contains any allergen species of concern.

In other embodiments, the analytical product can be a diagnostic device used to analyze human or animal samples. The device may be used to carry out multiple assay tests, including panels of assays for analytes or activities associated with a specific biochemical system, biochemical pathway, tissue, organism, cell type, organelle, disease state, class of receptors, class of enzymes; class of pathogen, environmental sample, food sample, etc. Other embodiments can comprise panels that include drugs of abuse, therapeutic drugs, auto-antibodies (e.g., one or more antibodies directed against the Sm, RNP, SS-A, SS-B Jo-1, and Scl-70 antigens), allergen specific antibodies, tumor markers, cardiac markers (e.g., one or more of Troponin T, Troponin I, myoglobin, CKMB, etc.), markers associated with hemostasis (e.g., one or more of Fibrin monomer, D-dimer, thrombin-antithrombin complex, prothrombin fragments 1 & 2, anti-Factor Xa, etc.), markers of fertility (e.g., one or more of Estradiol, progesterone, follicle stimulating hormone (FSH), luetenizing hormone (LH), prolactin, beta-hCG, testosterone, etc.), markers of congestive heart failure, markers of thyroid disorders, and markers of prostrate cancer (e.g., one or more of total PSA, free PSA, complexed PSA, prostatic acid phosphatase, creatine kinase, etc.), pathogens associated with upper respiratory infection (e.g., influenza A, influenza B, Respiratory Syncytial Virus, Streptococci species), pathogens found in food and water (e.g., *Salmonella, Listeria*, cryptosporidia, *Campylobacter, E. Coli* 0157, etc.), sexually transmitted diseases (e.g., HIV, syphilis, herpes, gonorrhea, HPV, etc.), blood borne pathogens and potential bioterrorism agents (e.g., pathogens and toxins in the CDC lists of Select A, B and C agents such as *B. anthracis, Y. pestis*, small pox, *F. tularensis*, ricin, botulinum toxins, staph enterotoxins, etc.).

An embodiment includes an analytical device that comprises
1) A sample region comprising a first opening and a first cavity within the device configured to receive a sample and closure means for covering the opening,
2) A second cavity comprising an extraction solvent or extraction reagent within the device,
3) An extraction region configured to receive at least a portion of the sample from the sample region and at least a portion of the extraction solvent,
4) A reaction region comprising one or more reaction reagents wherein the reaction region is located downstream of the extraction region and is configured to receive liquid flowing from the extraction region,
5) A first fluid passage connecting the extraction region to the reaction region wherein the first fluid passage comprises a first surface energy gradient coating,
6) A detection region comprising one or more detection agents wherein the detection region is located downstream of the reaction region and is configured to receive liquid flowing from the reaction region, and
7) A second fluid passage connecting the reaction region to the detection region wherein the second fluid passage comprises a second surface energy gradient coating.

An embodiment also includes a method of analyzing a sample for the presence of species of concern comprising the following steps:
1) Introducing a sample into the sample region of an analytical device and using closure means to enclose the sample within the device,
2) Contacting the sample with an extraction solvent wherein the extraction solvent extracts species of concern from the sample for a first target contact time
3) After the first target contact time has been reached, transferring the solution produced from the extraction solvent and the species of concern from the sample region through a first fluid passage comprising a first surface energy gradient coating to a separate reaction region comprising one or more reaction reagents,
4) Contacting the solution containing the species of concern with the one or more reaction reagents in the reaction region for a second target contact time to produce a solution comprising reaction products,
5) After the second contact time has been reached, transferring the solution comprising the reaction products from the reaction region through a second fluid passage comprising a second surface energy gradient coating to a detection region comprising one or more detection agents, 6) Contacting the solution comprising the reaction products with one or more detection agents in the detection region for a third target contact time to produce a detection response.

Figure 2:
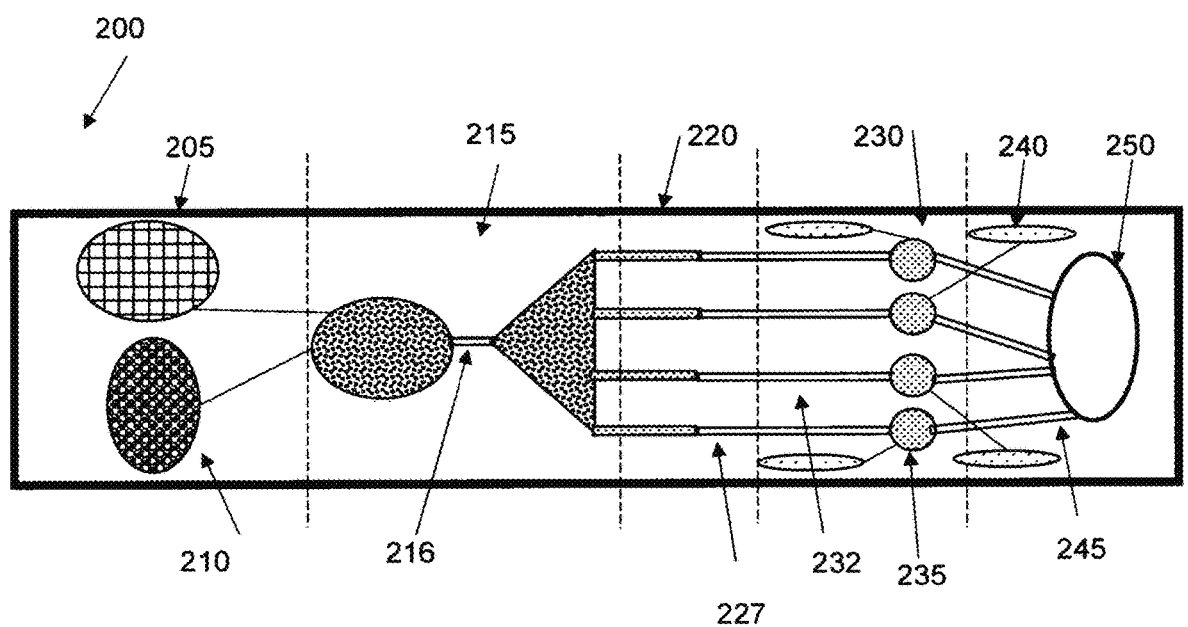
FIG. 2 is a drawing showing an embodiment of the disclosure.

FIG. 1 shows an embodiment of an analytical device 100 comprising a sample region 105, an extraction region 115, a reaction region 120, and a detection region 130 where reaction reagents are disposed on separate reaction wells 125. FIG. 2 shows an embodiment of an analytical device 200 comprising a sample region 205, an extraction region 215, a reaction region 220, and a detection region 230 where reaction reagents are disposed within the fluid passages 227.

The closure means of the device can include a screw cap, a threaded connection, a hinged or unhinged lid, a lid with a clamp, an o-ring or gasket fitting, or similar designs. The closure means can also include one or more features that also assist in breaking, straining, or grinding the sample up into smaller pieces to aid in extraction.

The extraction solvent 110 is stored in the product and can be in fluid communication with the sample region or a separate extraction region. The sample can be delivered to the extraction solvent at the location of the solvent or the solvent can be introduced to the sample at a separate location comprising an extraction region 115. The extraction solvent can also be added to the sample at a location where it also aids in breaking up the sample into a more extractable form. The solvent can be stored in a pierceable container and can be introduced to the sample after the container is pierced. The solvent maintains contact with the sample for a first target contact time to provide sufficient time to extract the species of concern. In embodiments, the first target contact time can be less than 20 minutes, less than 15 minutes, less than 10 minutes, less than 5 minutes, or less than 1 minute. The device can include additional features that improve mixing of the extraction solvent with the sample such as mixing regions, baffles, curved channels, or multiple intersection channels.

Surface energy gradient coatings can be used to control the contact time and flow rate of the liquids in the device. The first surface energy gradient coating in the first fluid passage 116 can be configured to provide controlled entry and flow through the fluid passage to ensure that the extraction solvent maintains contact with the sample for the first contact time so that a sufficient amount of the species of concern are extracted from the sample for further analysis. The first surface energy gradient coating can coat the entire length of the first fluid passage to provide a slow flow rate to the reaction region. In other embodiments, the first surface energy gradient coating can coat only a portion of the first fluid passage to provide an initial resistance to fluid entry (and additional hold-up in the extraction region) and relatively faster transfer through the first fluid passage to the reaction region.

The reaction region 120 can comprise reaction reagents in separate reaction wells 125, or the reaction reagents can be distributed along the walls of a fluid passage 227. The reaction region can also comprise additional on-board liquid reagents that flow to the reaction region to react with the liquid that flows from the extraction region to the reaction region. The reaction region can comprise a fluid passage with multiple openings along the channel's length that allow for the addition of reaction reagents to the liquid flowing from the extraction region along the length of the fluid passage. Surface energy gradient coatings can also be used in the fluid passages that deliver any liquid reaction reagents to the reaction region.

The second surface energy gradient coating in the second fluid passage 128 can be configured to provide controlled entry and flow through the fluid passage to ensure that the reaction reagents maintains contact with the solution flowing from the extraction region for the second target contact time so that a sufficient amount of reaction products are produced in the reaction region. The second surface energy gradient coating can coat the entire length of the second fluid passage to provide a controlled flow rate to the detection region. In other embodiments, the second surface energy gradient coating can coat only a portion of the second fluid passage to provide an initial resistance to fluid entry (and additional hold-up in the reaction region) and relatively faster transfer through the second fluid passage to the detection region. In embodiments, the second target contact time can be less than 20 minutes, less than 15 minutes, less than 10 minutes, less than 5 minutes, or less than 1 minute. The device can include additional features that improve mixing of the solution and reagents in the reaction region such as mixing regions, baffles, curved channels, or multiple intersection channels.

The detection region 130 can comprise detection reagents in separate wells 135, or the detection reagents can be distributed along the walls of a fluid passage 132. In embodiments, the detection reagents can bind to the reaction products in the solution and then be carried to a separate area where they are bound to a surface of the device. The detection region can also comprise additional on-board liquid reagents 140 that flow to the detection region to react with the liquid that flows from the reaction region to the detection region. The detection region can comprise a fluid passage with multiple openings along the channel's length that allow for the addition of detection reagents to the liquid flowing from the reaction region along the length of the fluid passage. The detection region can also comprise on-board rinse agents that flow to the region to remove any unbound species. Surface energy gradient coatings can also be used in the fluid passages that deliver any liquid detection reagents or rinses to the detection region.

In embodiments, the third target contact time can be less than 20 minutes, less than 15 minutes, less than 10 minutes, less than 5 minutes, or less than 1 minute. The device can include additional features that improve mixing of the solution and reagents in the reaction region such as mixing regions, baffles, curved channels, or multiple intersection channels. Surface energy gradient coatings can be used to control the flow rate of the liquid in the detection region to make sure the detection reagents have sufficient time to produce a detection response.

In some embodiments a third fluid passage 145 with a third surface energy gradient coating can be used to control the flow of liquid through the detection region. In embodiments, the third fluid passage is located downstream of the detection region and can be used to transfer liquid from the detection region to an overflow or waste area 150. The third surface energy gradient coating can coat the entire length of the third fluid passage to provide a controlled flow rate of liquid from the detection region. In other embodiments, the third surface energy gradient coating can coat only a portion of the third fluid passage to provide an initial resistance to fluid entry (and additional hold-up in the reaction region) and relatively faster transfer through the third fluid passage.

The reaction region and the detection region can comprise a strip or woven or nonwoven material that contains reaction reagents and/or detection reagents. Such materials can be used to wick liquid along the length and allow for species or concern to react with agents in the strip and be detected further downstream on the strip.

On-board solutions and chemical agents used in the extraction, reaction, or detection regions may be stored in pierceable containers. These containers may be pierced at the time the sample is closed into the device, or at a designated time after the sample is introduced into the device.

Figure 3:
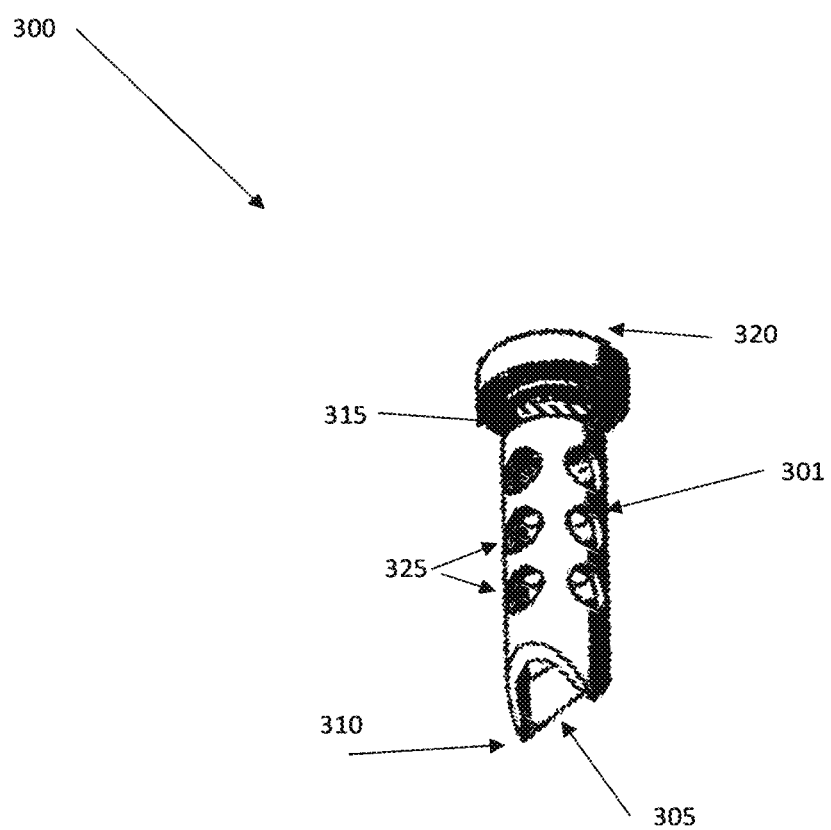
FIG. 3 is a drawing showing an embodiment of the sampler used with the product of the disclosure.

FIG. 3 shows an embodiment or a sampler 300 that could be used with the product of the disclosure. The sampler comprises a hollow tube 301 with an opening 305 on a proximal end 310 and a threaded end 315 on a distal end 320. The opening of the sampler can have a circular, oval, racetrack, or other cross-section shape. In an embodiment, the sampler can be used to obtain a food sample. To obtain a sample, the user can poke the sampler into one or more areas of the food sample so that the sample is collected inside the hollow tube. The proximal end of the sample can be angled to provide a sharper tip that aids in penetrating the food and collecting a food sample. The proximal end can also have saw-teeth or other protrusions along its radial edge to aid in collecting samples. The sampler can comprise one or more openings 325 along its axis from the distal end to the proximal end. In embodiments, the openings can be slot shaped. In other embodiments, the openings can comprise a circle or oval shape. The openings provide a means for the extraction solvent to contact the sample for the analysis. The distal end can also comprise an opening to aid in collecting liquid food samples.

Figure 4:
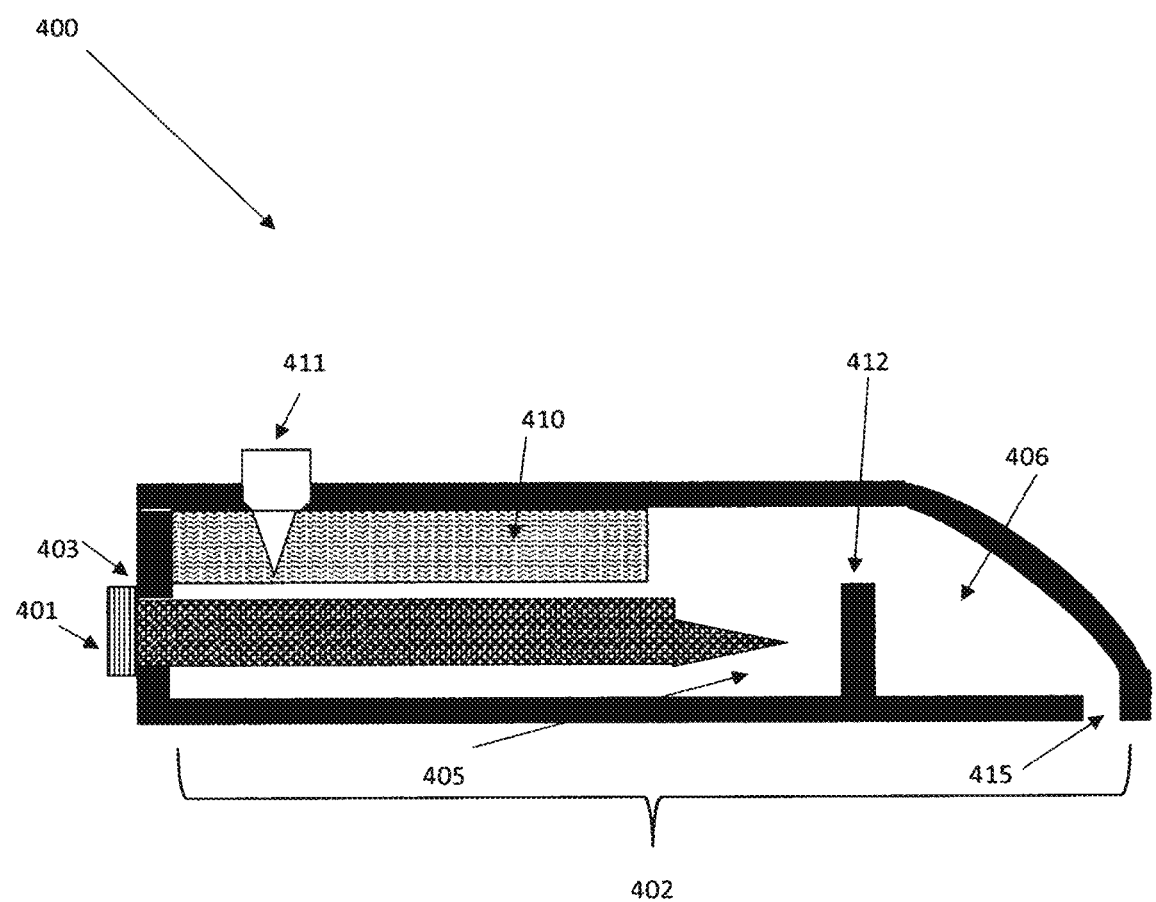
FIG. 4 is a drawing showing a view of an embodiment where the sampler is inserted into the product.

FIG. 4 shows a side view of a portion 400 of an embodiment where the sampler 401 with the food sample is enclosed in the extraction region 402. In this embodiment, the sampler is oriented in a horizontal direction relative to the bottom edge of the product (parallel to the bottom edge). The sampler is threaded into a threaded wall 403, sealing the sampler against the wall and enclosing the food sample inside the extraction region. The extraction region comprises a first region 405 and a second region 406. A pierceable container 410 positioned above the sampler comprises the extraction solvent. When the container is pierced, the extraction solvent flows over the sampler and contacts the food sample by flowing through the openings in the sampler. In an embodiment, a button 411 can be pressed by the user to pierce the container and start the flow of liquid. A short wall or baffle 412 within the extraction region can be used to partially contain the extraction solvent and extracted sample within the first region and provide additional contact time between the extraction solvent and food sample. As the liquid containing the extracted sample fills the first region and reaches the height of the baffle or wall, the liquid flows over the wall into a second region. An opening 415 in the second region provides a path for the liquid comprising the extracted sample to flow into reaction and detection regions (not shown) of the product. In an embodiment, a channel connects the second region of the extraction region to the reaction region. In an embodiment, the liquid flowing from the second region of the extraction region can flow into a well located upstream of the reaction region wherein a channel connects the well to the reaction region.

In embodiments, the sampler can be inserted vertically into the product. In embodiments, the sampler can comprise a threaded cap that screws around a connector on the product to seal. In embodiments, the proximal end of the sampler can comprise a hinged cap that closes over an opening to seal the sampler.

In embodiments, the sampler can comprise a protrusion that extends outward from the radius of the sampler and pierces the pierceable container when the sampler is enclosed into the product. In an embodiment, the distal end of the sampler can comprise a sharp tip or protrusion that pierces the pierceable container when the sampler is enclosed in the product.

In other embodiments, the sampler can be used to obtain samples from solid, semi-solid, or liquid materials. The sampler can comprise an absorbent material at one end for obtaining samples from a subject's mouth or nasal cavity. In an embodiment, the sampler can be used to obtain samples of human or animal tissue. In an embodiment, the sampler can be used to obtain samples of soil, water, or other environmental samples. In an embodiment, the sampler can be used to obtain samples of a biological material. In an embodiment, the sampler can be used to obtain samples of blood, plasma, or other bodily fluid. In an embodiment, the sampler can be used to take a sample of a manufactured material.

Figure 5:
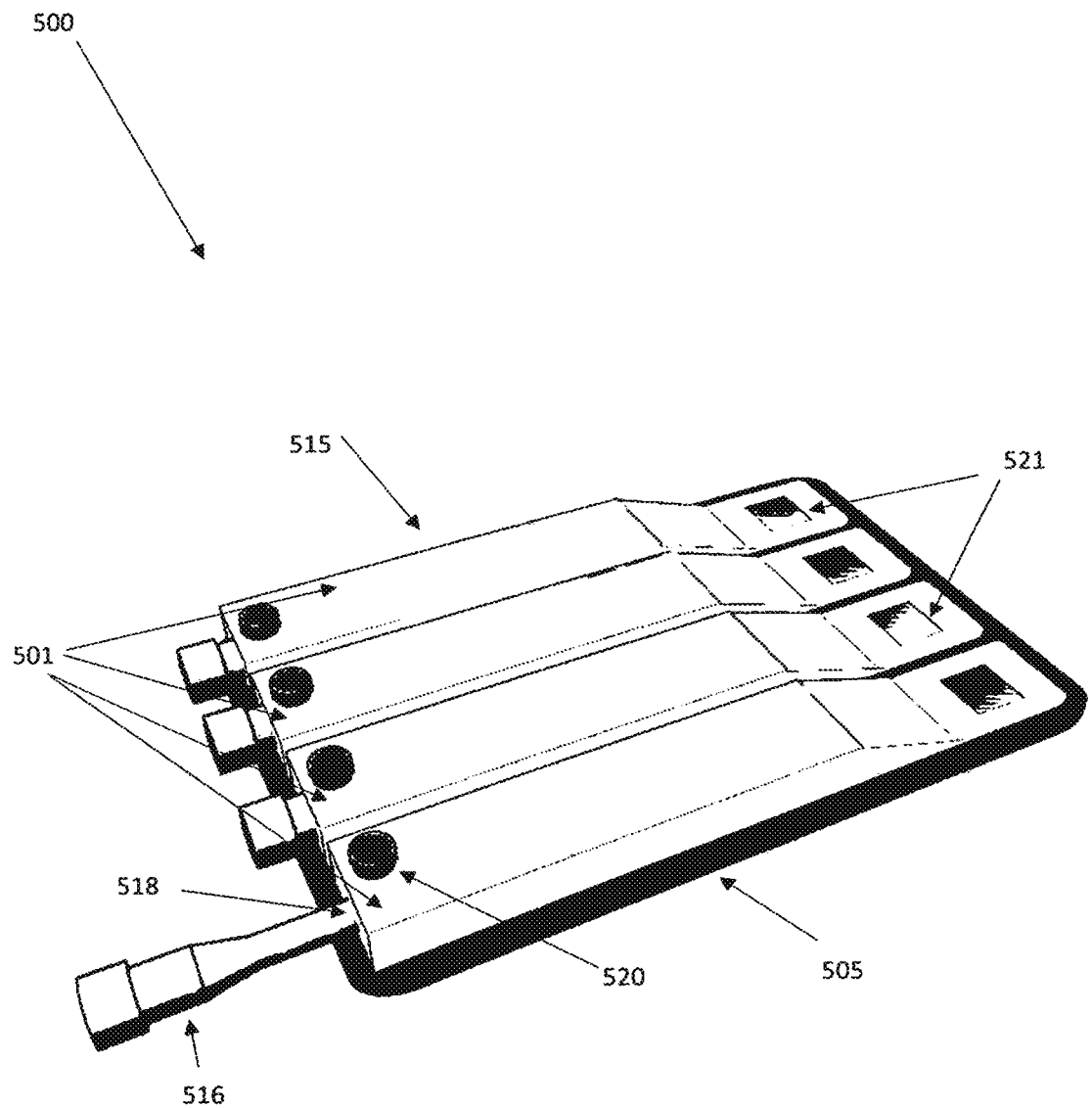
FIG. 5 is a drawing showing an embodiment that can analyze more than one sample.

FIG. 5 shows an embodiment of the disclosure wherein the product is a test card 500 comprising multiple individual test modules 501 that can run tests on more than one sample. In the figure, the test card can test up to four samples at one time or at separate times. Other card designs could have more or fewer test modules. The test card comprises a bottom layer 505, a channel layer, and a cover 515; in this view the channel layer is covered by the bottom layer and cover. The extraction region is bounded by the cover on the top and sides and the channel layer on the bottom. In the figure, the sampler 516 is inserted into the extraction region through the opening 518 located towards the bottom of the device and sealed. In this embodiment, each test module is separate from the other three test module; a separate sample is needed for each test, and each of the test modules runs a separate analysis. To start the analysis, the user pushes the button 520 above the sampler to pierce the container storing the extraction solvent. An opening or display window 521 in the cover allows the result in the detection region to be seen by the user.

Figure 6A:
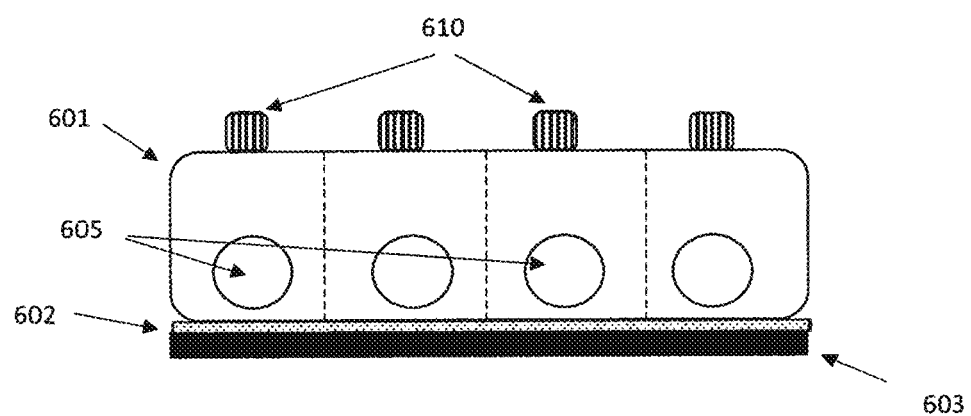
FIG. 6A is a drawing showing a view of an embodiment where portions of the product can be removed before or after testing.
Figure 6B:
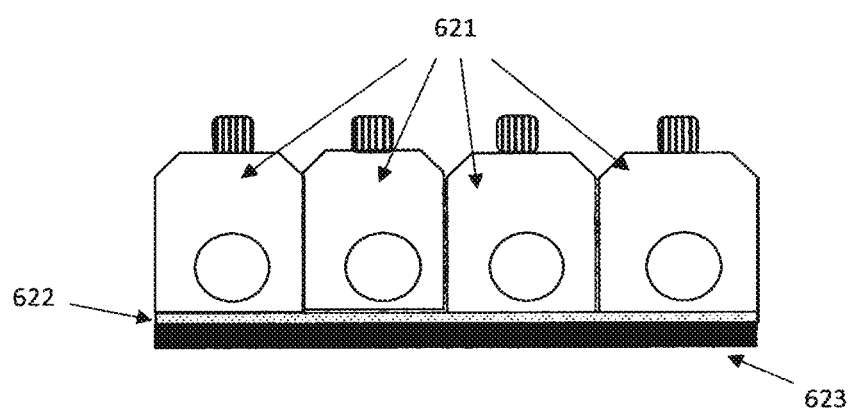
FIG. 6B shows another embodiment where portions of the product can be removed before or after testing.
Figure 6C:
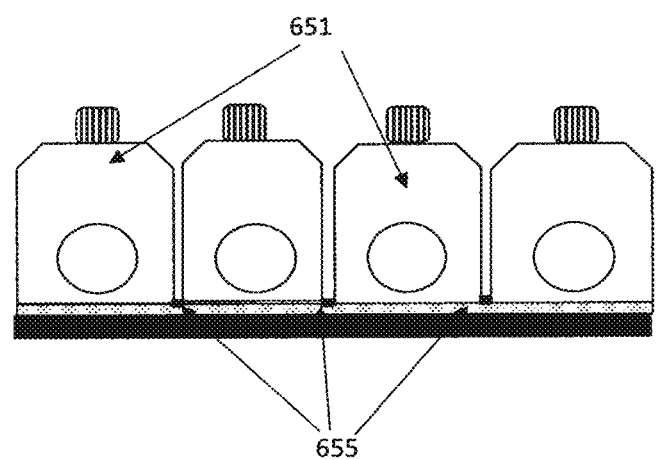
FIG. 6C shows a side view of another embodiment where portions of the product can be removed before or after testing.

A side view perspective showing features of an embodiment of the apparatus is shown in FIG. 6A. In the figure, the cover 601 is manufactured as a single piece for running the tests. Four tests are shown in the figure; other embodiments can run more or fewer tests. The cover is attached to one side of adhesive channel layer 602; a bottom layer 603 is attached to the other side of the channel layer. Openings 605 for the inserting the sampler for each test are shown along with button 610 that can be pushed to start the test. In other embodiments, each individual test module can be separated from the test card by the user before or after the analysis. FIG. 6B shows an embodiment where each cover piece 621 is manufactured separately and individually bonded to the channel layer 622. Perforations or cuts in the channel layer and/or the bottom layer 623 can be used to make it easier to separate modules from the test card. FIG. 6C shows a side view of an embodiment where the individual modules 651 can be separated from the test card. The cover can be molded as a single piece with thin sections 655 between test modules. The sections are thin enough so that each individual module can be broken off and separated from the other modules on the test card. Perforations or cuts in the channel layer and/or the bottom layer can be used to make it easier to separate modules from the test card. In other embodiments, separate cover pieces can be used for each module.

Figure 7:
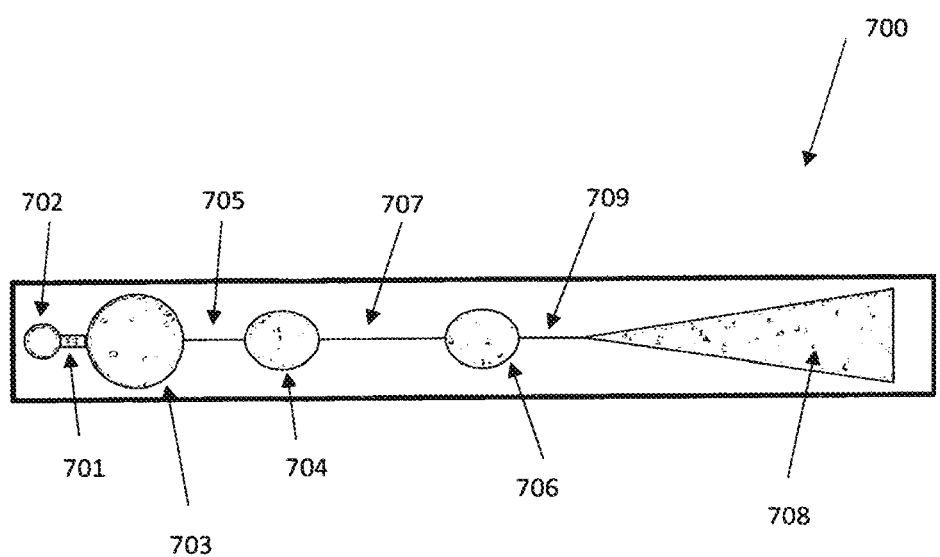
FIG. 7 is a drawing showing a top view of a channel layer design in an embodiment of the disclosure.

FIG. 7 shows a top view of a channel layer design in an embodiment of the disclosure. The flow from the extraction region can flow into the first of three wells. In an embodiment, the channel between the opening of the extraction region and the first well comprises a surface energy gradient coating. After the first well fills, the liquid flows into the second well which comprises reaction reagents that bind to the species of concern. In an embodiment, the species of concern is a food allergen. In an embodiment, the channel between the first well and the second well comprises a surface energy gradient coating. After the liquid has reacted with the reagents in the second well, it can flow into the third well which comprises detection reagents that bind to the species of concern. In an embodiment, the detection agent provides a visual cue such as a color change or fluorescence when the species of concern is detected. In an embodiment, the channel between the second well and the third well comprises a surface energy gradient coating.

FIG. 7 shows a top view 700 of a channel layer design in an embodiment of the disclosure. The flow from the extraction region can flow into the first of three wells. In an embodiment, the channel 701 between the opening 702 of the extraction region and the first well 703 comprises a surface energy gradient coating. After the first well fills, the liquid flows into the second well 704 which comprises reaction reagents that bind to the species of concern. In an embodiment, the species of concern is a food allergen. In an embodiment, the channel 705 between the first well and the second well comprises a surface energy gradient coating. After the liquid has reacted with the reagents in the second well, it can flow into the third well 706 which comprises detection reagents that bind to the species of concern. In an embodiment, the detection agent provides a visual cue such as a color change or fluorescence when the species of concern is detected. In an embodiment, the channel 707 between the second well and the third well comprises a surface energy gradient coating. A storage region 708 located downstream of the detection region can be used to collect and store the liquid used in the test. The shape of the storage region can be designed as a trapezoidal shape to enhance capillary flow into the region. The channel 709 between the detection region and the storage region can comprise a surface energy gradient coating.

Figure 8:
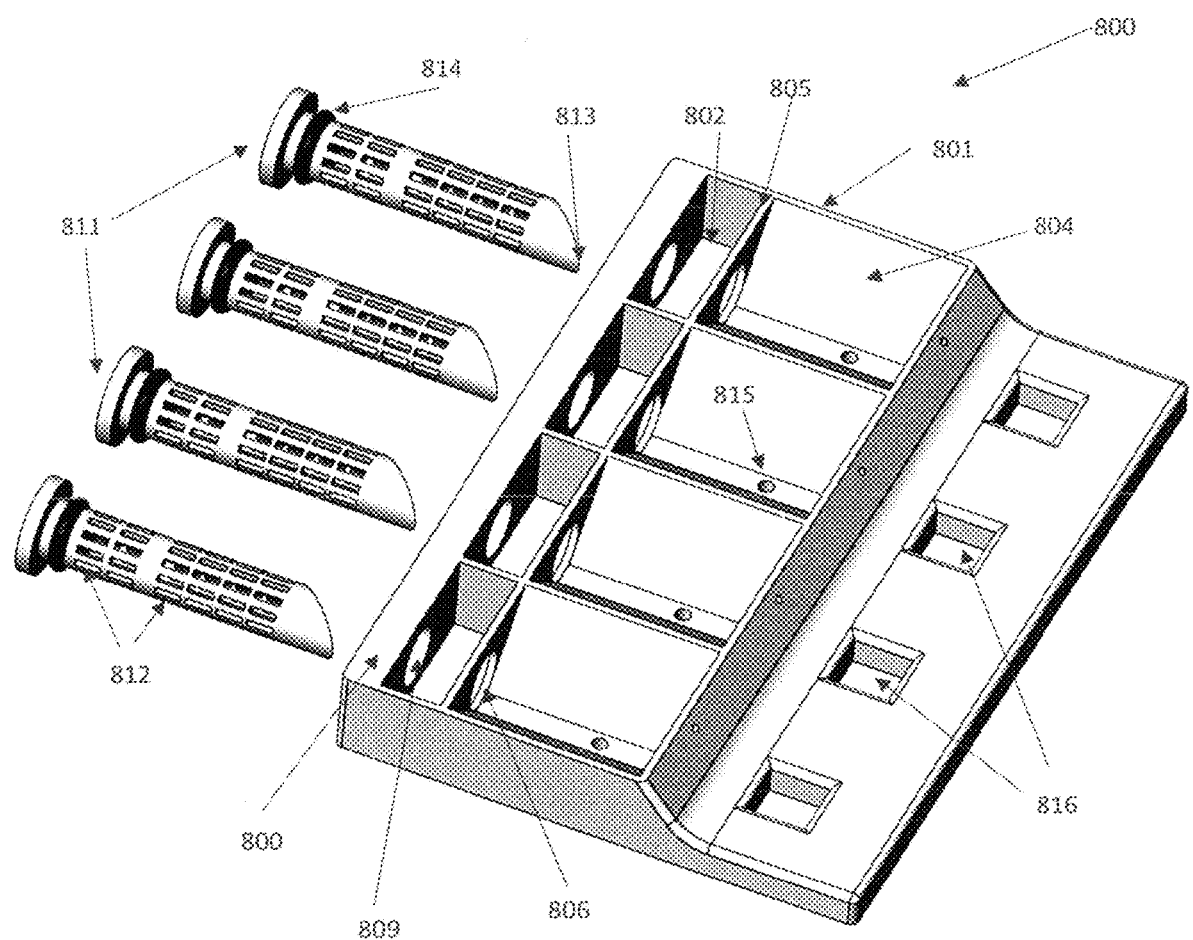
FIG. 8 is a drawing which shows the interior of the top cover of an embodiment of the disclosure.

Another embodiment of the analytical device is shown in FIG. 8, which shows the interior of the top cover. In this embodiment, a button is not required to start the test. Instead, the test is started when the user loads the sample into the top cover. The interior 801 of the top cover 800 of the device comprises a first chamber 802 comprising an extraction solvent 803 and a second chamber 804 adjacent to the first chamber. The first chamber and the second chamber are enclosed within the top cover of the device. A first wall or other partition 805 can separate the first chamber from the second chamber. The first wall between the first chamber and second chamber can comprise a first opening 806. The first opening can be covered with a material 807 that prevents the extraction solvent in the first chamber from flowing into the second chamber. A second wall or partition 808 can separate the first chamber from the environment outside the analytical device. In an embodiment, the second wall comprises an outside wall of the top cover. The second wall can comprise a second opening 809. The second opening can be covered with a material 810 that prevents the extraction solvent in the first chamber from leaking outside the device. In embodiments, the material used to cover the first and second openings comprises a foil seal. In embodiments, the material used to the cover the first and second openings comprises a polymer seal. In embodiments, the material used to cover the first and second openings is thinner than the first wall. In embodiments, the material used to cover the first and second openings can be punctured without damaging the first or second wall. In embodiments, the material used to cover the first or second opening is sealed to the wall using an adhesive. In an embodiment, the material used to cover the first or second opening is welded to the wall.

To test a sample, a sampler 811 is used to collect the sample. The sampler can comprise a hollow tubular shape that extends from a proximal end to a distal end. The sampler comprises one or more slots or openings 812 in the sampler's wall along its length. In embodiments, the open area of the outside surface area of the sampler can be between 20 and 80 percent. The distal end of the sampler can comprise a tip or protrusion 813 that extends along its axial length. The proximal end of the sampler can comprise an O-ring 814 or other fitting for sealing the sampler against the second wall of the top cover when the sampler is inserted through the second opening in the second wall. The sampler can be pressed into the food or material at one or more locations to collect a sample of the food or material inside the hollow tube. The tip or protrusion in the sample can aid in sample collection by allowing the sampler to be inserted into food or material sample more easily than a flat edge could be inserted. In embodiments, the sampler can also include reverse barbs on the inside radius to help hold sample material in place.

After the food or material sample has been collected inside the sampler, the sampler is then inserted into the first and second openings in the first and second walls of the top cover. The tip or protrusion can be used to help pierce the material covering the first and second openings. When inserted, the proximal end of the sampler is sealed against the second wall. The sampler extends fully through the first chamber and at least a portion of the sample extends into the second chamber. The extraction solvent in the first chamber contacts the food or material sample by flowing into the openings in the sampler wall. The extraction solvent flows along the axial length of the sampler and into the second chamber through the openings in the portion of the sampler that extends into the second chamber. The extraction solvent can continue to contact the food or material sample in both the first chamber and the second chamber. After contacting the food or material sample for sufficient time to extract the species of concern from the sample, the solvent can then flow out of the second chamber through one or more holes 815 located on the bottom surface of the second chamber. Results of the analysis can be displayed in the viewing window 816. FIG. 8 shows an embodiment with four tests on a device. Additional embodiments can comprise a lesser or greater number of tests. In embodiments each single test can be separated from the other tests before or after each analysis is done.

In embodiments, the process to manufacture the cover comprises an injection molding process. In an embodiment, the process to manufacture the cover comprises an additive manufacturing process. In an embodiment, the cover comprises a polymer. In an embodiment, the cover comprises a ceramic. In an embodiment, the cover comprises a metal.

In embodiments, the test card comprises a cover, a channel layer, and a bottom layer wherein the cover is bonded to at least a portion of the channel layer, the channel layer is bonded to at least a portion of the bottom layer, and the channel layer is positioned between the cover and the bottom layer. In an embodiment, the test card comprises a cover and a bottom layer wherein the cover comprises the wells and channels defining the liquid flow path and the cover is bonded to at least a portion of the bottom layer.

In embodiments, the process to manufacture the sampler comprises an injection molding process. In an embodiment, the process to manufacture the sampler comprises an additive manufacturing process. In an embodiment, the sampler comprises a polymer. In an embodiment, the sampler comprises a ceramic. In an embodiment, the sampler comprises a metal.

An embodiment includes an analytical device that comprises the following:
1) A sample region comprising a first opening and a first cavity within the device configured to receive a sample and closure means for covering the opening,
2) A second cavity comprising an extraction solvent or extraction reagent within the device,
3) An extraction region configured to receive at least a portion of the sample from the sample region and at least a portion of the extraction solvent,
4) A reaction region comprising one or more reaction reagents wherein the reaction region is located downstream of the extraction region and is configured to receive liquid flowing from the extraction region,
5) A first fluid passage connecting the extraction region to the reaction region wherein the first fluid passage comprises a first surface energy gradient coating,
6) A detection region comprising one or more detection agents wherein the detection region is located downstream of the reaction region and is configured to receive liquid flowing from the reaction region.
7) A separate sampler holder for a sampler comprising a storage compartment located above the extraction region.

The sampler holder can comprise a storage compartment and be integrated with the device for improved convenience. The storage compartment can store the sampler in an enclosed space that keeps the sampler clean and uncontaminated prior to use. The user can remove the sampler from the storage compartment, take a sample of the material he or she wants to analyze, and then insert the sampler into the extraction region of the device for extraction and analysis. In an embodiment, the storage compartment is not in fluid communication with the extraction region of the device while the sampler is stored inside the storage compartment. In an embodiment, the sample holder is located adjacent to the extraction region of the device. In an embodiment, the sample holder is located above the extraction region of the device.

The sampler can comprise a first portion and a second portion wherein the first portion is configured to collect a sample and the second portion comprises sealing means to seal against the opening of the second compartment. The first portion of the sampler can be a variety of shapes including cylindrical, oval, rectangular. The outer radius or edges of the first portion can comprise openings that allow for liquid to pass into the sampler and drain out of the sampler after species have been extracted. The openings in the first portion can provide the first portion of the sampler with an open area of between 10 and 90 percent. The first portion of the sampler can have an open area of no less than 30 percent. The first portion of the sampler can have an open area of no less than 50 percent. The openings in the first portion can be a variety of shapes including circular, oval, rectangular, or other shape. The second portion of the sampler can use a variety of sealing methods. The closure means of the device can include a screw cap, a threaded connection, a hinged or unhinged lid, a lid with a clamp, an o-ring or gasket fitting, or similar designs. The seal can be either an axial seal or a radial seal. In some embodiments, the seal can comprise an adhesive. The sealing means of the second portion can be selected from the group consisting of an O-ring, a threaded cap, a press-fit seal, a gasket, and a cap closure.

An embodiment of the disclosure can be an analytical device comprising
1) A first sealed compartment comprising an extraction solvent or extraction reagent within the device wherein the first compartment comprises a seal over an opening,
2) A second compartment comprising an opening, wherein the opening of the second compartment is aligned with the opening of the first compartment,
3) A reaction region comprising one or more reaction reagents wherein at least a portion of the reaction region is located below at least a portion of the first or second compartment and is configured to receive liquid flowing from the first or second compartment.
4) A first fluid passage connecting the first or second compartment to the reaction region wherein the first fluid passage comprises a first surface energy gradient coating,
5) A detection region comprising one or more detection agents wherein the detection region is located downstream of the reaction region and is configured to receive liquid flowing from the reaction region.
6) A third compartment having an opening wherein at least a portion of the third compartment is located above the reaction region, and
7) wherein the openings of the first, second, and third compartments are configured to receive at least a portion of a sampler.

The first surface energy gradient coatings can comprise species X1-J1-M1 and species X2-J2-M2 wherein X1, X2, M1, and M2 represent separate functional groups where M1 and M2 have different surface energies and J1 and J2 represents spacer moieties, and the molar concentration of the species X2-J2-M2 increases relative to the molar concentration of the species X1-J1-M1 in the gradient surface energy coating from the first or second compartment to the reaction region. The analytical device can comprise additional fluid passages that connect additional reagents to other regions of the device. In embodiments the additional fluid passages can comprise surface energy gradient coatings. The composition of the surface energy gradient coatings can be different in each fluid passage. In an embodiment, the analytical device can comprise a fluid passage connecting the reaction region to the detection region. In an embodiment, the device can have additional compartments that store either dry or liquid reagents. These additional compartments can be connected with fluid passages to other regions of the device, such as the detection or reaction regions. The additional compartments can include wash reagents that can be used to remove unbound species from the detection or reaction regions. The additional compartments can include additional reagents that can react further with the liquid being analyzed. The additional compartments can also include reagents that change the physical properties of the liquid being analyzed such as colorants, viscosity modifiers, or other modifiers. The additional compartments can be sealed and the seal can be broken during use. In other embodiments, the compartments can be open to the flow of the liquid being analyzed.

Additional embodiments of the analytical device can include the following:
The reaction region comprises at least a portion of a lateral flow strip. The lateral flow strip can also be used in the detection region. Separate lateral flow strips can be used in the reaction and detection regions.

The analytical device can comprise a second fluid passage connecting the reaction region to the detection region wherein the second fluid passage comprises a second surface energy gradient coating. The second surface energy gradient coating can comprise species X1-J1-M1 and species X2-J2-M2 wherein X1, X2, M1, and M2 represent separate functional groups where M1 and M2 have different surface energies and J1 and J2 represents spacer moieties, and the molar concentration of the species X2-J2-M2 increases relative to the molar concentration of the species X1-J1-M1 in the gradient surface energy coating from the reaction region to the detection region.

The analytical device can comprise a fourth compartment comprising a liquid reagent and a fluid passage connecting the fourth compartment to the detection region or reaction region. The second fluid passage comprises a second surface energy gradient coating. The second surface energy gradient coating can comprise species X1-J1-M1 and species X2-J2-M2 wherein X1, X2, M1, and M2 represent separate functional groups where M1 and M2 have different surface energies and J1 and J2 represents spacer moieties, and the molar concentration of the species X2-J2-M2 increases relative to the molar concentration of the species X1-J1-M1 in the gradient surface energy coating from the fourth compartment to the reaction or detection region.

The analytical device can have compartments sized to hold all or portions of the sampler. The device can include an integrated sampler holder that comprises a compartment sized to fit the sampler and keep the first portion of the sampler clean and uncontaminated prior to use. This compartment can be adjacent to the extraction, reaction, or detection regions of the device. The location of the sampler holder can vary depending on the overall design of the device. The sampler can seal against one or more walls of the compartment. The seal can be either an axial or radial seal.

The analytical device can be designed with compartment that together are able to enclose all or portions of the sampler. In an embodiment, the device can comprise a sealed compartment holding a liquid that is adjacent to an empty compartment with the seal separating the empty compartment from the liquid-filled compartment. During use, the sampler can be inserted into one or both compartments and break the seal between them. Liquid can flow into the sampler to extract the species of interest while the portion of the sampler holding the sample is enclosed in both compartments and the sampler seals against one or more walls of either compartment. The seal can be either an axial or radial seal.

Figure 9:
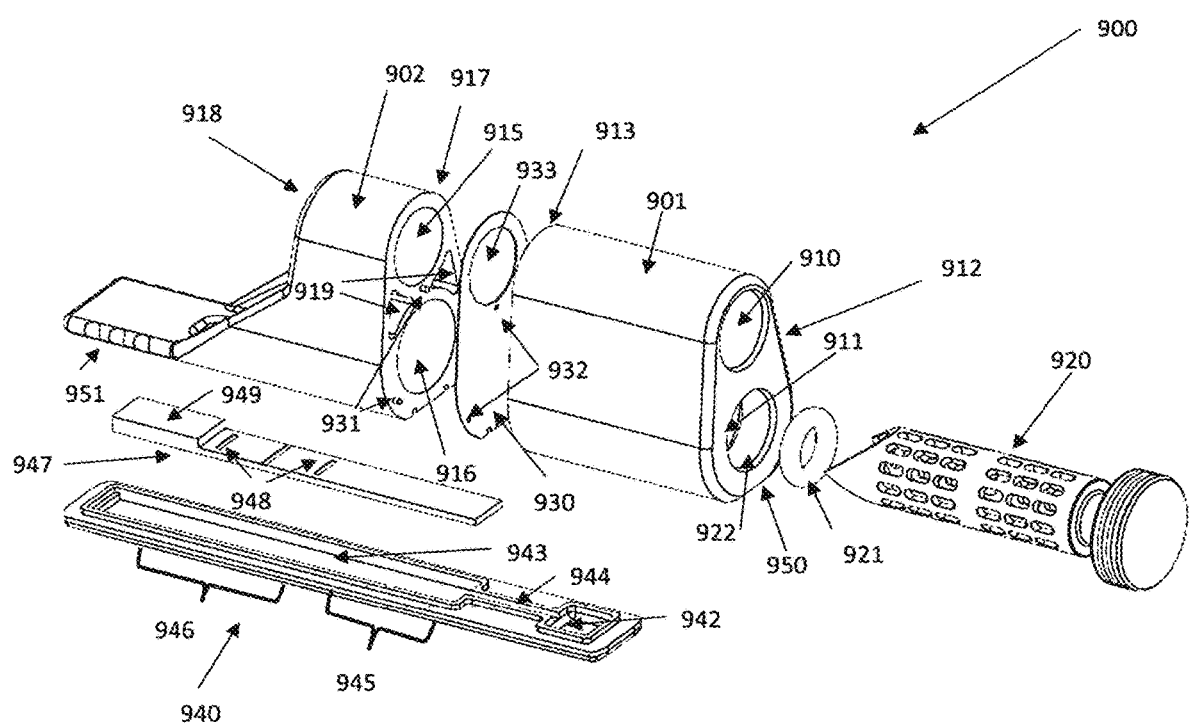
FIG. 9 is a drawing of an embodiment with a different configuration showing components of the embodiment.
Figure 10:
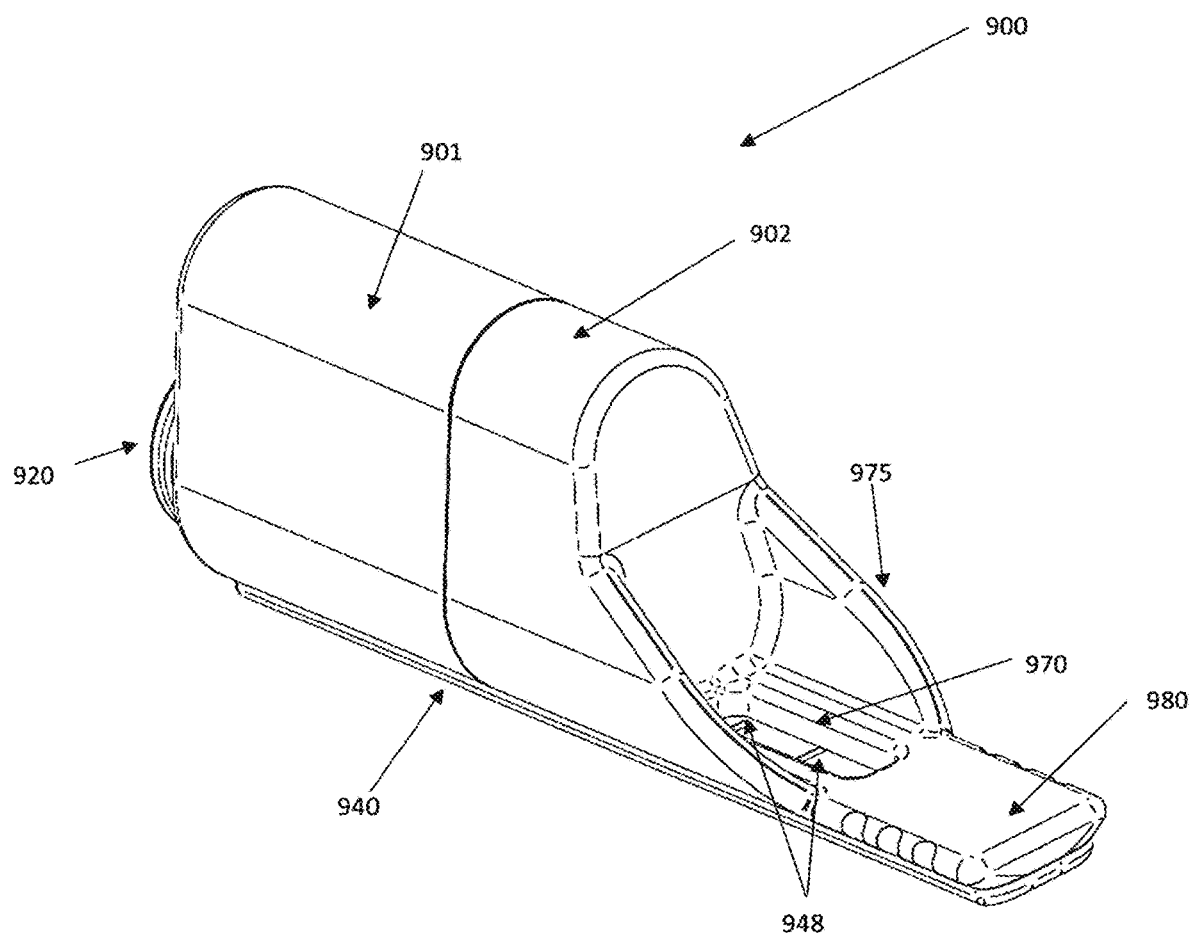
FIG. 10 is a drawing showing a view of the embodiment with the sampler inserted.
Figure 11:
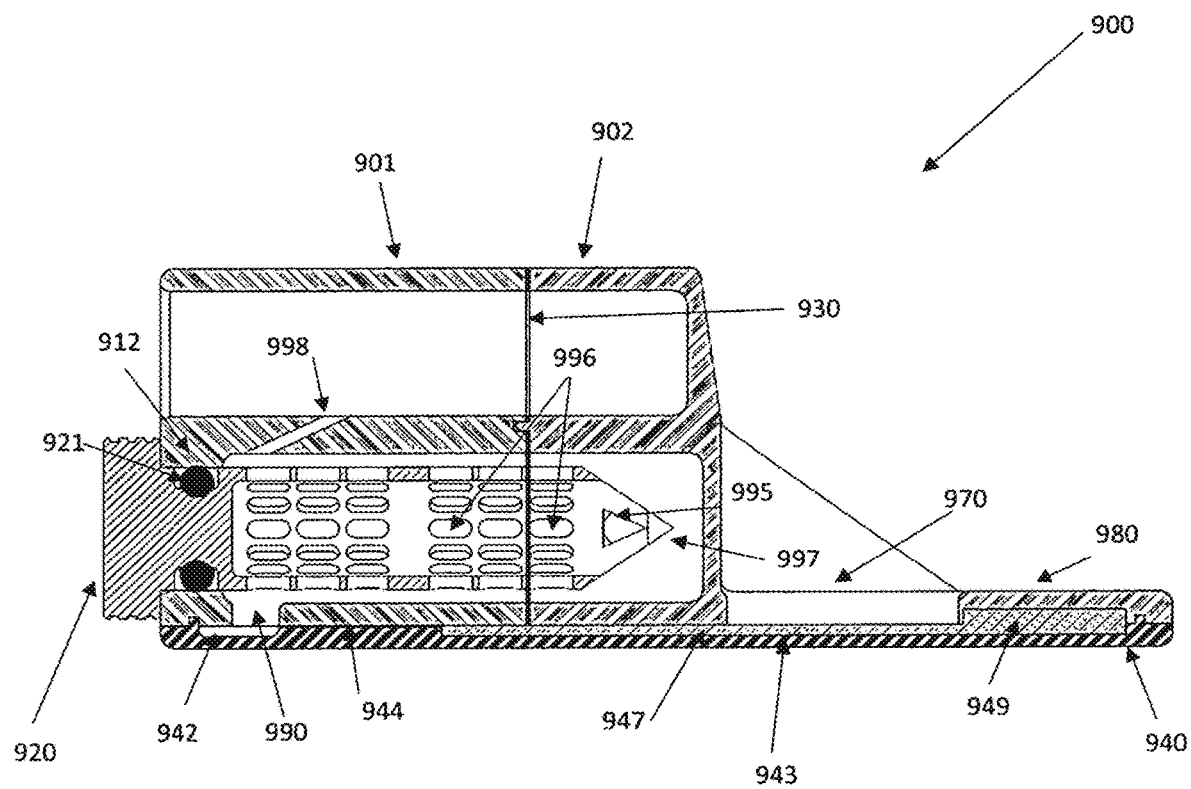
FIG. 11 is a drawing showing a cross-sectional view of the embodiment with the sampler inserted.

FIG. 9-11 show views for an embodiment of a device with a sampler holder storage comprising a storage compartment for the sampler integrated into the device; the figures also illustrate an alternative construction and configuration of the device components. In FIG. 9, the components of the device 900 are shown in an exploded view. First component 901 comprises a top chamber 910 and a bottom chamber 911 with openings at a first end 912 that both extend all the way through the first component's length to a second end 913. Both openings are sized to fit sampler 920. In embodiments, the sampler comprises a cylindrically-shaped portion with openings along its exterior radius. In an embodiment, an o-ring 921 can be used to seal the sampler against the wall 922 of chamber 911 to form a liquid-proof seal. Other sealing methods such as threaded fittings with a gasket or washer, snap closures, or other methods could be used. In embodiments, the sampler and o-ring form can form a seal in chamber 910. Second component 902 comprises a top closed chamber 915 and a bottom closed chamber 916 with openings at a first end 917. The openings do not extend all the way through component 902. The second side 918 of the second component does not have openings, forming the closed chambers 915 and 916. Optional hollow portions 919 can be used in first component 901 or second component 902 to reduce the amount of material used in the product or provide additional flexibility if desired.

Components 901 and 902 are designed fit together so that chamber 910 of first component 901 and closed chamber 915 of second component 902 form a storage region for holding the sampler. The storage region can be used to hold the sampler before using the product to do any analysis. First component 901 and second component 902 also fit together so that chamber 911 and closed chamber 916 can also form a combined region. A gasket 930 can be used between the components to form a liquid-proof seal. Optional pins 931 on second to component 902 can be aligned with matching holes on first component 901 to provide for better alignment and sealing of the two components. The pins can pass through openings 932 on the gasket to align the gasket properly between the two components and help seal them together properly. The gasket can comprise an adhesive on both sides. The gasket can contain an opening 933 that allows the sampler to be stored in the storage area comprised of chamber 911 and 915. The gasket initially provides separation between closed chamber 916 and chamber 911 and also forms a liquid-proof seal. The entire gasket can comprise a material that can be pierced by the sampler, or portions of the gasket that cover the openings for chamber 911 and closed chamber 916 can be thinner or comprise a different material as the rest of the gasket so that the sampler can pierce through it.

Third component 940 of device 900 comprises a first compartment 942 that is configured to receive solution to be analyzed. In some embodiments, this compartment can also comprise additional reagents to react with one or more species in a solution. A channel 944 connects the compartment 942 to a second compartment 943. Channel 944 can comprise a surface energy gradient coating on one or more of its surfaces to control the flow from compartment 942 to compartment 943 so that the extraction solvent has sufficient time to extract a species of interest from the sample. Second compartment 943 comprises reaction agents at a proximal site 945 and detection agents at a distal site 946 for reacting with and detecting species in a solution. In an embodiment, second compartment 943 is configured to store a lateral flow strip 947 wherein the lateral flow strip comprises a region storing reaction agents at a proximal location and a region storing detection agents at a distal location. In embodiments, the reaction agents can comprise coated beads or particles. In embodiments the detection agents can be dispersed in one or more lines 948 that span the width of the lateral flow strip. In embodiments, the lateral flow strip can also comprise an absorbent pad 949. Third component 940 is designed to seal against the bottom edge 950 of first component 901 and the bottom edge 951 of second component 902. In embodiments, an adhesive, gasket, or other sealing material may be used to help seal third component 940 to first component 901 and second component 902.

FIG. 10 shows an additional view of device 900 after first component 901, second component 902, and third component 940 have been assembled together and the sampler 920 has been inserted to perform an analysis. Second compartment 902 comprises a viewing window 970 for observing the results of the analysis. The presence or absence of lines 948 in the viewing window can be used to determine the results of the analysis. Optional support material 975 can be added to provide additional strength and stiffness to the product. The second component 902 can also comprise a tab 980 that extends past the viewing window.

FIG. 11 shows a cross-sectional view of the device 900 after first component 901, second component 902, and third component 940 have been assembled together and the sampler 920 has been inserted to perform an analysis. The o-ring 921 around the sampler helps form a seal against the wall 912 of the bottom chamber of first component 901. When the sampler is inserted for analysis, it pierces through the gasket 930 into the bottom chamber of second component 902. This chamber contains an extraction solvent 1000 used to remove species of interest from the sample held by the sampler. The sampler can comprise a sharp tip 995 along the radius at the end of the sampler to aid with piercing the gasket as well as with obtaining a sample. The sampler can also comprise one or more reverse barbs 997 at different locations along its interior radius to aid in collecting the sample. As the sampler contacts the extraction solvent, the solvent can contact the sample in the sampler by flowing through openings 996 located along the wall of the sampler as well as through the open end of the sampler. As the extraction solvent contacts the food sample, it can flow out of the sampler through openings in the sample wall and into the bottom chamber of first component 901. The device can include a vent passage 998 for allowing air to escape as the liquid flows into the chamber. The liquid exiting the sampler into the bottom chamber of the first component 901 will comprise the extraction solvent and any species of interest that the extraction solvent removed from the sample. An opening 990 at the bottom of the chamber allows the liquid to flow down and fill the compartment 942 of third component 940. The surface energy gradient coating on channel 944 limits initial flow out of the compartment 942, giving the extraction solvent sufficient contact time to extract species of interest from the sample. Once sufficient contact time has been allowed for the extraction, the liquid flows to the lateral flow strip 947 contained inside compartment 943. The detection region in the lateral flow strip is aligned with the viewing window 970 so that the user can easily view the results of the analysis. The lateral flow strip can include a control line, a detection line, and an overload line. The absorbent pad 949 can be aligned under the tab 980.

The overall length, width, and height dimensions of the device can be designed to provide convenience and discretion for the user. A plurality of individual test devices can be combined in a package. Individual test devices can be separated and disposed of after use. In an embodiment, the product is a single test product with a height no more than 25 mm. In an embodiment, the product is a single test product with a length no more than 125 mm. In an embodiment, the product is a single test product with a width no more than 50 mm. In an embodiment, the product is a single test product with a height between 2 and 25 mm, a length between 25 and 100 mm, and a width between 4 and 25 mm. In an embodiment, the product comprises a plurality of individual test products and has an overall height no more than 25 mm. In an embodiment, the product comprises a plurality of individual test products and has an overall length no more than 125 mm. In an embodiment, the product comprises a plurality of individual test products and has an overall width no more than 100 mm. In an embodiment, the product comprises a plurality of individual test products and has an overall length between 25 and 100 mm, and overall width of between 15 and 75 mm, and an overall height between 2 and 20 mm.

In an embodiment, the device is configured to store no more than 2 mL of an extraction solvent. In another embodiment, the device is configured to store no more than 1 mL of an extraction-solvent. In another embodiment, the device is configured to store no more than 0.5 mL of an extraction solvent. In an embodiment, the device is configured to store no less than 0.1 mL of an extraction solvent. In an embodiment, the device is configured to store no less than 0.4 mL of an extraction solvent. In an embodiment, the device is configured to store no less than 1 mL of an extraction solvent.

In an embodiment, the sampler is configured to collect a sample volume of no more than 1 cubic centimeters. In an embodiment, the sampler is configured to collect a sample volume of no more than 0.5 cubic centimeters. In an embodiment, the sampler is configured to collect a sample volume of no more than 0.2 cubic centimeter. In an embodiment, the sampler is configured to collect a sample volume of no more than 0.1 cubic centimeter. In an embodiment, the sampler is configured to collect a sample volume of no more than 0.02 cubic centimeter. In an embodiment, the sampler is configured to collect a sample volume of no less than 0.01 cubic centimeters. In an embodiment, the sampler is configured to collect a sample volume of no less than 0.1 cubic centimeters. In an embodiment, the sampler is configured to collect a sample volume of no less than 0.5 cubic centimeters. In an embodiment, the sampler is configured to collect a sample volume of no less than 1 cubic centimeters.

In an embodiment the surface is a nonwoven material or a film or other flexible material. In an embodiment, the nonwoven material or film comprises a metallic coating such as aluminum, nickel, gold, silver, copper, or other materials. Multiple methods can be used to apply metallic coatings to different film or nonwoven surfaces. In an embodiment, a channel comprises a flexible film comprising a surface energy gradient coating.

EXAMPLES

An embodiment of the analytical product using a top cover design depicted in FIG. 8 was manufactured. Additive manufacturing was used to produce the samplers and the top cover 800; the sampler and cover components were manufactured using FLGPCL04 clear resin polymer. The first compartment 801 was sized to store 500-ul of phosphate buffer solution. An adhesive foil layer 9472LE (5-mil thickness) from 3M was used to separate the first compartment and second compartment in the top cover. The bottom layer of the device was made of 5-mil thick Duralar Polyester film and was attached to the top cover using a 3M AR 90106 film as an adhesive channel layer. The channel region in the bottom component had length, width, and height dimensions of 4500-um, 800-um, and 100-um respectively. A lateral flow strip configured to detect gluten was used in the device. A surface energy gradient coating was deposited on the bottom surface of the channel 944 to control the flow rate of the liquid to 3-5 minutes (0.9-1.5 mm/min). The samplers had an inner radius of 4.8 mm and an outer radius of 6.3 mm with an interior volume of ~0.125 cubic centimeters; the openings on the sampler were ~4-mm×2-mm and the open area of the outer radius of the sampler was ~50%. The overall length of each sampler was 33 mm. The overall dimensions of the product were 55-mm length, 85 mm width, and 12 mm height.

An embodiment of the analytical product depicted in FIGS. 9-11 was manufactured. Additive manufacturing was used to produce the sampler and the first component 901, second component 902, and third component 940. All components were manufactured using Makerbot Specialty PETG polymer resin. The first compartment 901 had an interior volume of 0.6 cubic centimeters and could store 500-ul of phosphate buffer solution. An adhesive foil layer (3M 9472LE, 5-mil thickness) was used to seal the first compartment and second compartment. The channel region in the bottom component had length, width, and height dimensions of 8 mm, 2 mm, and 100 um respectively. Component 940 was attached to the first and second components using a 3M AR90106 as an adhesive channel layer. A lateral flow strip configured to detect gluten was used in the device. A surface energy gradient coating was deposited on the bottom surface of the channel 944 to control the flow rate of the liquid to 2-5 minutes (1.6-4 mm/min). The sampler had an inner diameter of 7.1 mm and an outer radius of 8.6 mm; the holes on the sampler were ~3.6 mm in diameter, and the open area along the outside radius of the sampler was ~50%. The sampler was sized to hold a sample size of 0.125 cubic centimeters. The overall length of the sampler was 32 mm. The overall dimensions of the product were 56 mm length, 14 mm width, and 22-mm height.

An embodiment also includes a method of analyzing a sample for the presence of species of concern comprising the following steps:

1) Introducing a sample into the sample region of an analytical device and enclosing the sample within the device,
2) Contacting the sample with an extraction solvent wherein the extraction solvent extracts species of interest from the sample for a first target contact time
3) After the first target contact time has been reached, transferring the solution produced from the extraction solvent and the species of interest from the sample region through a first fluid passage comprising a first surface energy gradient coating to a separate reaction region comprising one or more reaction reagents,
4) Contacting the solution containing the species of concern with the one or more reaction reagents in the reaction region for a second target contact time to produce a solution comprising reaction products,
5) After the second contact time has been reached, transferring the solution comprising the reaction products from the reaction region to a detection region comprising one or more detection agents,
6) Contacting the solution comprising the reaction products with one or more detection agents in the detection region for a third target contact time to produce a detection response.

In embodiments, the detection response can be visually observed by the user. In other embodiments, the detection response can be captured by a camera or other optical sensor. In embodiments, the detection response can be captured by an electrochemical sensor.

In an embodiment, the extraction solvent comprises an aqueous solvent. In an embodiment, the extraction solvent comprises a buffer solution. The buffer solution can be a phosphate buffer solution. The pH of the solvent can be between 5 and 9. In embodiments, the extraction solvent comprises one or more species to improve the extraction and/or detection of a substance. In an example for gluten detection, the extraction solution can contain 2-mercaptoethanol, or tris(2-carboxyethyl)phosphine, which operates by reducing disulfide prolamin crosslinking in a sample, and solubilizes proteins in the sample to facilitate detection. The extraction solution can additionally or alternatively contain guanidine hydrochloride, or N-lauroylsarcosine, or other disaggregating agents. In variations for other allergens, the extraction solution can comprise ethanol for a dairy-derived allergen (e.g., lactose), a parvalbumin extraction solution for a fish-derived allergen, an ara-h2 extraction solution for a nut derived allergen, an egg protein extraction solution for an egg-derived allergen (e.g., ovomucoid protein, ovalbumin protein, ovotransferrin protein, lysozyme protein), a tropomyosin extraction solution for a shellfish-derived allergen, and/or any other suitable extraction solution for any other harmful substance.

In embodiments, the device can also comprise one or more reagent solutions. In embodiments, variations of the reagent(s) can additionally or alternatively include any one or more of: a reagent for lysing of a sample, a reagent for solubilization of a sample, a reagent for buffering of a sample, a reagent for dilution of a sample, and any other suitable reagent(s). In embodiments, the one or more reagent solutions can comprise a wash solution that removes unbound species from the reaction or detection region.

For fluid passages with a rectangular cross-section, the capillary pressure within a channel can be predicted by the following equation.

$$P = gam/h * (\cos(thet1) + \cos(thet2) - (2*h/w)) \qquad \text{Eq 1}$$

where
P=Pressure
gam=surface tension of the liquid
h=channel height, distance between top and bottom surfaces
thet1=contact angle between liquid and bottom surface
thet2=contact angle between liquid and top surface
w=width of channel To initiate flow into a channel, the capillary pressure must be greater than 0. As can be seen from the equation, capillary pressure is a function of the contact angle the liquid forms with the top and bottom surfaces, the channel dimensions, and the liquid surface energy. Each of these parameters can be adjusted to control the entrance of a liquid into a capillary channel. Similar equations for different geometric shapes and varying cross-sections can be derived. A graph of capillary pressure as calculated in Equation 1 as a function of contact angle will show that the relationship between capillary pressure and contact angle is approximately linear for contact angle values between 30 and 130 degrees. This relationship indicates that velocity can be controlled within a channel by changing the contact angle in a controlled manner. Using the equations for drag in a capillary channel along with equation 1 for calculating the capillary pressure, coating compositions can be configured to produce controlled surface energy gradient coatings that can be used to provide a controlled, or even constant, fluid velocity over the length of a channel. Coatings can be configured to control liquid flow by providing coating compositions that control the initial contact angle at the beginning of the channel, by providing coating compositions that change the contact angle over the length of the channel, and by providing coating compositions that increase or decrease the rate of change of the contact angle over the length of the channel. The degree of the surface energy gradient can be changed by changing the coating composition over the length of the channel. For example, a coating could be configured on one channel surface that would provide a contact angle of 100 degrees at the entrance to a channel and that would then reduce the contact angle by 10 degrees every 5 mm for a given length of the channel. To increase or decrease the velocity in different channels, coatings can be configured that change the rate of the contact angle change over the length of the channel—to provide a higher fluid velocity, the rate of change in the contact angle per length could be increased; to provide a lower fluid velocity, the rate of change in the contact angle could be decreased. Average liquid velocity in the fluid channels due to the change in capillary pressure provided by the surface energy gradient can be varied from a low of 0 mm/s to more than 15 cm/s depending on the fluid properties and the channel dimensions. In embodiments, the average fluid velocity can be over 30 cm/s. The average fluid velocity can also be increased further by increasing the liquid head pressure from the fluid.

Microfluidic products can be created by many known methods including machining, micromolding, embossing, additive manufacturing, thermoforming, injection molding, laser-etching, chemical etching, UV-exposure, chemical or physical deposition, etc. These methods can also be used to create the flow passages and wells configured to allow liquid flow through the device. Components and sub-assemblies of the microfluidic products can be produced by one or more manufacturing method and then combined with other components and sub-assemblies manufactured by a different method. For the invention many possible materials can be used as the material for the microfluidic products of the invention; suitable materials include PTFE, polycarbonate, polypropylene, polyethylene, PDMS, polyester, nylon, PMMA, COC polymer, acrylic, glasses, metals, ceramics, etc. The microfluidic products of the invention can be fabricated using other different manufacturing methods, such as photolithography techniques, micromachining technology, or additive manufacturing. Such methods that may be used to fabricate channels, substrates, and products according to the invention are well known in the art and include film deposition processes, such as spin coating and chemical vapor deposition, laser fabrication or photolithographic techniques, or etching methods, which may be performed either by wet chemical or plasma processes.

Microfluidic products may be constructed using different manufacturing techniques. For example, the microfabrication methods used to make microchips in the computer industry may also be used to create microfluidic products, enabling the creation of intricate, minute patterns of interconnected channels. Once a pattern is created, microchip manufacturing methods can be employed to recreate the channel design on a surface, layer, or component of the microfluidic product. In some instances, chemical etching or stamping techniques can be employed. As a result, highly precise channels with dimensions that can be varied in their width and depth may be produced. Once the pattern is produced, a cover plate can be affixed or sealed over the surface so as to form conduits in combination with the channels.

Different solid substrate materials may be used in practice of the present invention. For example, useful substrates may be opaque, translucent, clear, textured, patterned, rough, smooth, rigid, flexible, treated, primed, or a combination thereof. The substrate typically comprises organic and/or inorganic material. The substrate may be, for example, thermoplastic, thermoset, or a combination thereof. Exemplary substrates include films, plates, tapes, rolls, molds, sheets, blocks, molded articles, fabrics, and fiber composites (e.g., circuit boards), and may comprise at least one organic polymer such as polyimide, polyester, acrylic, polyurethane, polyether, polyolefin (e.g., polyethylene or polypropylene), polyolefin-copolymer, polyamide, and combinations thereof. Exemplary inorganic substrates include metals (e.g., chromium, aluminum, copper, nickel, silver, gold, steel, and alloys thereof), ceramics, glass, china, quartz, polysilicon, and combinations thereof. For microfluidic products comprised of laminated layers, each layer can comprise a different substrate material. The product can comprise a plurality of layers. In embodiments, the plurality of layers comprises a first layer and a second layer wherein the first layer comprises a different polymer than the second layer. In embodiments, the plurality of layers comprises a first layer and a second layer wherein the first layer comprises the same polymer as the second layer. In embodiments, the fluid passages of the microfluidic products can be located at any position within the cartridge and oriented at any angle. In an embodiment, the fluid passages are located, primarily, in planar networks, located proximate to the outside surfaces to allow for a multi-layered cartridge design that uses, e.g., machined, die-cut, laser-cut and/or molded cartridge body component. In embodiments, fluid passage geometries include passages with cross-sections that are circular, oval, square or rectangular in cross-section. Width and height of the fluid passages can vary widely from nm to cm ranges depending on the application, sample volume and cartridge design. Ranges for the height are 0.02 to 2 mm, preferably, 0.05 to 1.5 mm, most preferably 0.05 mm to 1 mm.

The fluidic network may be formed within the device in a number of different ways, dependent, in part, upon the materials chosen for the device. Any known fabrication method appropriate to the device body material may be employed including, but not limited to, stereolithography, chemical/laser etching, integral molding, machining, lamination, etc. Such fabrication methods may be used alone or in combination. In certain embodiments of the invention, the device comprises a body and one or more cover layers mated to surfaces of the body so as to define one or more fluidic networks preferably, planar fluidic networks) therebetween. Similarly, z-transitions and/or ports can be selectively molded into, or machined out of, the body at predetermined locations to form the fluidic connections between the fluid passages on the upper and lower surfaces.

One embodiment of the device may be fabricated using a "lamination" process whereby laminated layers are used to form the fluidic network. For example, recesses (e.g., channels, grooves, wells, etc.) can be manufactured into one or more surfaces of the device body to provide a recessed pattern of the fluidic network. Sealing/mating of the recessed patterns to cover layers forms a fluidic network comprising fluidic components (e.g., conduits, chambers, etc.) at least some of which are defined in part by the recesses in the device and in part by a surface of a cover layer. In an embodiment, the cover layers are comprised of plastic film. The cover layer may be coated with an adhesive to seal the cover layer against the device body. Other methods for mating the cover layer to the body will be known to the skilled artisan, e.g., the seal may be achieved by heat sealing, ultrasonic welding, RF (radio frequency) welding, by solvent welding (applying a solvent between the components that softens or partially dissolves one or both surfaces), by use of an intervening adhesive layer (e.g., a double sided adhesive tape, etc.). Features that are created by patterned deposition (e.g., patterned deposition of electrode or dielectric layers and/or patterned deposition of reagents to form dry reagent pills or to form binding domains with immobilized binding reagents) can created on cover layers so as to take advantage of automation available to process plastic film in large sheets or rolls.

Recesses may be, e.g., molded in, etched in or machined from the device body. By analogy, fluidic components may also be defined, at least in part, by recesses in a cover layer that is mated to the device body. Fluidic components may also be defined, at least in part, by regions cutout from gasket layers disposed between the device body and cover layers. Apertures in the device body and/or cover layers may be used to provide for vent ports, reagent addition ports and the like. Vent ports can be used to allow the equilibration of fluid in the chambers with the atmosphere or to allow for the directed movement of fluid into or out of a specified chamber by the application of positive or negative pressure. Vent ports are designed to prevent the leakage of liquid samples or reagents through the ports and may include aerosol-resistance filters, membrane or filter materials that permit air flow but act as barriers to liquid solutions and materials that are porous to air but seal when they come in contact with solutions.

The products of the invention can comprise a surface comprising a glass, metal, metal oxide, or polymer surface. In an embodiment, the surface is a metal oxide comprising a metal oxide from the group comprising silica, alumina, quartz, glass, or the like and the coating configured to control liquid flow comprises carboxylic acid moiety. In an embodiment, the base surface is a metal selected from the group comprising gold, silver, copper, cadmium, zinc, palladium, platinum, mercury, lead, iron, chromium, manganese, tungsten, and any of their alloys, and the coating comprises a sulfur-containing moiety (e.g. thiols, sulfides, disulfides, and the like). In another embodiment, the surface is doped or undoped silicon and the coating comprises a silane or chlorosilane species. In another embodiment, the surface is a metal selected from the group comprising palladium and platinum and the coating comprises a nitrites or isonitrile species. In an embodiment, the surface is copper and the coating comprises a hydroxamic acid species. In another embodiment, the surface is gold and the coating comprises at least one sulfur-containing functional group selected from the group comprising thiols, sulfides, or disulfides. In an embodiment, the product of the invention comprises a surface comprising a cyclic olefin copolymer.

In embodiments, the surfaces of the fluid passages can comprise polymeric species selected to exhibit one or more properties desired for the surface or other substrate to which the polymer molecules are bonded. In embodiments, the coating configured to control liquid flow in the microfluidic product can comprise polymeric species selected to exhibit one or more properties desired for the surface or other substrate to which the polymer molecules are bonded. For example, it may be desired in some instances to provide polymeric species with very hydrophilic properties, in which case polymer species such as hyaluronic acid may be employed. The polymer polyethylene glycol may be employed to repel proteins from a surface. Heparin, a polysaccharide, may be used to impart antithrombogenic characteristics, and chitosan may be employed to provide hemostatic properties. In another embodiment, the polymer species comprises ionic, nonionic, polar, nonpolar, halogenated, alkyl, aryl or other functionalities.

In embodiments, the compounds used to form the coating compositions for the coating configured to control liquid flow can have the general formula X-J-M where X represents a species that forms the bond to the surface, J represents a spacer moiety or polymer backbone species, and M represents a functional group that is provided to the surface of the coating. Species X1, X2, . . . Xn can be selected based on the surface materials and bonding requirements desired. Species J1, J2, . . . Jn can be selected based on the properties of the polymer chain desired, including chain length, film stability, cross-linking capabilities, reactivity, etc. Species M1, M2, . . . Mn can be selected based on the surface energy properties desired as well as other functional properties desired including reactivity, adsorption, bonding, etc. In embodiments, multiple n solutions comprising compounds of Xn-Jn-Mn can be used. In embodiments, X-J-M compounds can form self-assembled monolayers from solution.

In embodiments, the functional group M1, M2, . . . Mn is selected from the group comprising ionic, nonionic, polar, nonpolar, halogenated, alkyl, aryl or other functionalities, In other embodiments, the functional group M1, M2, . . . Mn can include any one of the following: —OH, —CONHR, —CONHCOR, —NHR, —COOH, —COOR, —CSNHR, —COR, —RCSR, —RSR, —ROR, —SOOR, —RSOR, —CONR$_2$, —(OCH$_2$ CH$_2$)$_n$OH, —(OCH$_2$ CH$_2$)$_n$OR —CH$_3$, —NR$_2$, —CN, —(CF$_2$)$_n$CF$_3$, —CO$_2$CH$_3$, —CONHCH$_3$, —CR, CHCH$_2$, —OCH$_2$CF$_2$CF$_3$, Cl, Br, olefins, and the like; and any combination thereof.

In the above list, R is hydrogen or an organic group such as a hydrocarbon or fluorinated hydrocarbon. As used herein, the term "hydrocarbon" includes alkyl, alkenyl, alkynyl, cycloalkyl, aryl, alkaryl, aralkyl, and the like. The hydrocarbon group may, for example, comprise methyl, propenyl, ethynyl, cyclohexyl, phenyl, tolyl, and benzyl groups. The term "fluorinated hydrocarbon" is meant to refer to fluorinated derivatives of the above-described hydrocarbon groups.

In another embodiment, J is a hydrocarbon chain with the formula —(CH$_2$)$_n$— where n is between 1 and 22, preferably between 2 and 18, more preferably between 2 and 12. In some embodiments using metal oxide base surfaces, the functional group X is a carboxylic acid.

In an additional embodiment, the base surface is a metal selected from the group comprising gold, silver, copper, aluminum, cadmium, zinc, palladium, platinum, mercury, lead, iron, chromium, manganese, tungsten, and any alloys of the above. In some embodiments using metals for the base surfaces, the functional group X is a sulfur-containing functional group (e.g. thiols, sulfides, disulfides, and the like). In other embodiments, the metal of the base surface is in the form of a metalized film coating a polymer surface.

In another embodiment, the base surface is doped or undoped silicon. In some embodiments using doped or undoped silicon for the base surface, the functional group X is selected from the group comprising silanes or chlorosilanes. In another embodiment, the base surface is a metal selected from the group comprising palladium and platinum. In some embodiments using these metals for the base surface, the functional group X is a functional group selected from the group comprising nitrites and isonitriles. In another embodiment, the base surface is copper. In some embodiments using copper for the base surface, the functional group X is a hydroxamic acid. In another embodiment, the base surface is gold. In some embodiments using gold for the base surface, the functional group X is at least one sulfur-containing functional group selected from the group consisting of thiols, sulfides, or disulfides.

In some preferred embodiments, at least one of the molecules of formula (X-J-M) chosen to form the coating configured to control liquid flow is resistant to the adsorption of biopolymers such as proteins, enzymes, antibodies, polynucleic acids, cells, and other biological molecules. By the term "resistant to the adsorption of biopolymers" it is meant that the base surface covered by the coating has a reduction in the amount of a biopolymer adsorbed on the surface, when contacted with a medium containing biopolymers available for adsorption, as compared to the amount adsorbed on the same base surface that is not covered by the coating. In some embodiments, the coating configured to control liquid flow is a monolayer.

For some embodiments, the J group of the molecule is a spacer moiety comprising a biopolymer-resistant domain. Suitable moieties for the biopolymer-resistant domain of the J group are discussed in U.S. Pat. No. 6,235,340 and include oligoethers, oligoglycols, oligoalcohols, oligocarbonyls, oligosulfides, oligosulfones and oligosaccharides. Such moieties typically are used to produce a monolayer or other coating that is both hydrophilic and biopolymer-resistant.

In one embodiment, the biopolymer-resistant domain comprises an oligo-(ethylene glycol) linkage ($-OCH_2CH_2-$)$_n$, where n is 2 to 4.

The surfaces of the fluid passages or the coating configured to control liquid flow may use polymers that are natural or synthetic in origin. Such polymers include oligomers, homopolymers and copolymers resulting from addition or condensation polymerization, and natural polymers including oligosaccharides, polysaccharides, peptides, and proteins. The polymers may include several distinct polymer types, as prepared by terminal or side chain grafting The polymers of the invention may include cellulose-based products such as hydroxyethyl cellulose, hydroxypropyl cellulose, carboxymethyl cellulose, cellulose acetate and cellulose butyrate, acrylics such as those polymerized from hydroxyethyl acrylate, hydroxyethyl methacrylate, glyceryl acrylate, glyceryl methacrylate, acrylic acid, methacrylic acid, acrylamide and methacrylamide, vinyls such as polyvinyl pyrrolidone and polyvinyl alcohol, nylons such as polycaprolactam, polylauryl lactam, polyhexamethylene adipamide and polyhexamethylene dodecanediamide, polyurethanes, polylactic acids, linear polysaccharides such as amylose, dextran, chitosan, and hyaluronic acid, and branched polysaccharides such as amylopectin, hyaluronic acid and hemi-celluloses.

In an embodiment, the surfaces of the fluid passages can comprise latent reactive (e.g., photoreactive) groups bonded to the surface itself. In an embodiment, the coating configured to control liquid flow can comprise latent reactive (e.g., photoreactive) groups bonded to the surface itself. For instance, with ceramic or glass surfaces, a photoreactive silane can be used. Similarly, with surfaces of gold or other noble metals, an intermediate layer can be provided using a photoreactive sulfur compound (e.g., thiol or thioether such as methyl thioxanthone) or other suitable compound. In another embodiment, a SAM (self-assembled monolayer) can be formed at a suitable interface, and optionally transferred to a solid support surface. The surface, in turn, can be provided by a material selected from ceramics, metals and polymeric materials. For instance, the surface can be provided by a material selected from organosilane-pretreated glasses, organosilane-pretreated silicon materials, and silicon hydrides, or by a polymeric material selected from the group consisting of polystyrene, polycarbonate, polyester, polyethylene, polyethylene terephthalate (PET), polyglycolic acid (PGA), polyolefin, poly-(p-phenyleneterephthalamide), polyphosphazene, polypropylene, polytetrafluoroethylene, polyurethane, polyvinyl chloride, polyacrylate (including polymethacrylate), and silicone elastomers, as well as copolymers and combinations thereof.

The surfaces of the fluid passages and/or the coating configured to control liquid flow can comprise a photoreactive group. Photoreactive groups respond to specific applied external stimuli to undergo active specie generation with resultant covalent bonding to an adjacent chemical structure, e.g., as provided by the same or a different molecule. Photoreactive groups are those groups of atoms in a molecule that retain their covalent bonds unchanged under conditions of storage but that, upon activation by an external energy source, form covalent bonds with other molecules. Upon activation of the photoreactive groups, the reagent molecules are covalently bound to each other and/or to the material surface by covalent bonds through residues of the photoreactive groups. The photoreactive groups generate active species such as free radicals and particularly nitrenes, carbenes, and excited states of ketones upon absorption of electromagnetic energy. Photoreactive groups may be chosen to be responsive to various portions of the electromagnetic spectrum, and photoreactive groups that are responsive to e.g., ultraviolet and visible portions of the spectrum are preferred and may be referred to herein occasionally as "photochemical group" or "photogroup". Latent reactive groups can be chosen that are responsive to various portions of the electromagnetic spectrum, with those responsive to ultraviolet and visible portions of the spectrum (referred to herein as "photoreactive") being particularly preferred. In an embodiment, the coating can provide latent reactive groups to the surface, for instance, wherein the surface comprises a ceramic, silicon oxide, metal oxide, or glass surface, and the coating comprises a photoreactive silane.

Photoreactive aryl ketones, such as acetophenone, benzophenone, anthraquinone, anthrone, and anthrone-like heterocycles (i.e., heterocyclic analogs of anthrone such as those having N, O, or S in the 10-position), or their substituted (e.g., ring substituted) derivatives may be used in the coating configured to control liquid flow. The functional groups of such ketones are readily capable of undergoing the activation/inactivation/reactivation cycle described herein. Benzophenone is a preferred photoreactive moiety, since it is capable of photochemical excitation with the initial formation of an excited singlet state that undergoes intersystem crossing to the triplet state. The excited triplet state can insert into carbon-hydrogen bonds by abstraction of a hydrogen atom (from a support surface, for example), thus creating a radical pair. Subsequent collapse of the radical pair leads to formation of a new carbon-carbon bond. If a reactive bond (e.g., carbon-hydrogen) is not available for bonding, the ultraviolet light-induced excitation of the benzophenone group is reversible and the molecule returns to ground state energy level upon removal of the energy source. In an embodiment, the surface comprises a polymer surface and the coating comprises a photoreactive aryl ketone. Additional photoreactive groups include azides. The azides constitute a class of photoreactive groups and include arylazides such as phenyl azide and particularly 4-fluoro-3-nitrophenyl azide, acyl azides such as benzoyl azide and p-methylbenzoyl azide, azido formates such as ethyl azidoformate, phenyl azidoformate, sulfonyl azides such as benzenesulfonyl azide, and phosphoryl azides such as diphenyl phosphoryl azide and diethyl phosphoryl azide. Diazo compounds constitute another class of photoreactive groups and include diazoalkanes such as diazomethane and diphenyldiazomethane, diazoketones such as diazoacetophenone and 1-trifluoromethyl-1-diazo-2-pentanone, diazoacetates such as t-butyl diazoacetate and phenyl diazoacetate, and beta-keto-alpha-diazoacetates such as t-butyl alpha diazoacetoacetate. Other photoreactive groups include the diazirines such as 3-trifluoromethyl-3-phenyldiazirine, and ketenes such as ketene and diphenylketene.

The surfaces of the fluid passages and/or the coatings configured to control liquid flow may contain one or more thermochemically reactive groups (i.e., groups having a reaction rate dependent on temperature). Suitable groups are selected from the group consisting of activated esters, epoxide, aziactone, activated hydroxyl and maleimide groups. Those skilled in the art would also recognize numerous other amine-reactive functional groups such as isocyanates, thioisocyanates, carboxylic acid chlorides, epoxides, aldehydes, alkyl halides and sulfonate esters, such as mesylate, tosylate and tresylate, each of which could serve as the thermochemically reactive group. Optionally, the coating can also contain one or more photoreactive groups. Additionally, the coating may comprise one or more hydrophilic polymers, to which the thermochemically reactive and/or photoreactive groups can be pendent. The photoreactive groups (alternatively referred to herein as "photogroups") can be used, for instance, to attach molecules to the surface of the support upon the application of a suitable energy source such as light. The thermochemically reactive groups, in turn, can be used to form covalent bonds with appropriate and complementary functional groups on a different molecule. In another embodiment, the coating can comprise self-assembling monolayer molecules wherein the self-assembling monolayer molecules themselves provide thermochemical reactive groups and the method comprises the further step of attaching binding molecules to the monolayer by reaction between corresponding reactive groups of the binding molecules and the reactive groups of the self-assembling monolayer molecules.

Coating compositions can be configured to produce controlled surface energy gradient coatings that can be used to provide a controlled, or even constant, fluid velocity over the length of a channel. By providing different individual channels with different coating compositions, the surface energy gradient can be varied in each channel, resulting In different linear velocities for the fluid in individual channels. This feature allows for a slow reaction or process to take place in a first channel and a faster reaction or process to take place in a second channel, all on the same layer of the microfluidic product while keeping the same length, width, and height dimensions for the first and second channel. In some cases, serpentine paths and other long flow paths can be eliminated from the design of the microfluidic product, resulting in simpler manufacturing designs and smaller overall product dimensions. Using coatings providing surface energy gradients, linear velocities for liquids such as water in the range of 0-30 cm/s can be achieved for microfluidic channels. In an embodiment, linear velocity for the fluid in a first channel is greater than 0.5 mm/sec while linear velocity for the fluid in a second channel is less than 0.1 mm/sec. In embodiments, the linear velocity for fluid in a first channel can be no less than 1 mm/min. In embodiments, the linear velocity for fluid in a first channel can be no less than 5 mm/min. In embodiments, the linear velocity for fluid in a first channel can be no less than 25 mm/min. In embodiments, the linear velocity for fluid in a first channel can be no less than 50 mm/min. In embodiments, the linear velocity for a fluid in a second channel can be no greater than 25 mm/min. In embodiments, the linear velocity for a fluid in a second channel can be no greater than 25 mm/min. In embodiments, the linear velocity for a fluid in a second channel can be no greater than 15 mm/min. In embodiments, the linear velocity for a fluid in a second channel can be no greater than 5 mm/min. In embodiments, the linear velocity for a fluid in a second channel can be no greater than 1 mm/min.

The composition of the coating as well as the channel dimension can be adjusted based on the particular liquid used and the liquid properties including viscosity, density, surface tension, and the contact angle the liquid forms with the coating or surface to configure the coating to provide flow control for many different microfluidic systems using many different fluids. Preferred methods and materials for creating coatings will vary for many reasons including the substrate used for the surface, the chemical species selected, the surface activation method chosen, cost, fluid solutions selected, and operating conditions for the process. The surfaces of the fluid channels can comprise coated and uncoated regions.

I claim:

1. An analytical device comprising
  A) A first sealed compartment comprising an extraction solvent or extraction reagent within the device wherein the first sealed compartment comprises a seal over an opening,
  B) A second compartment comprising an opening, wherein the opening of the second compartment is aligned with the opening of the first compartment,
  C) A reaction region comprising one or more reaction reagents wherein at least a portion of the reaction region is located below at least a portion of the first or second compartment and is configured to receive liquid flowing from the first or second compartment,
  D) A first fluid passage connecting the first or second compartment to the reaction region wherein the first fluid passage comprises a first surface energy gradient coating,
  E) A detection region comprising one or more detection agents wherein the detection region is located downstream of the reaction region and is configured to receive liquid flowing from the reaction region,
  F) A third compartment having an opening wherein at least a portion of the third compartment is located above the reaction region, and
  wherein the openings of the first, second, and third compartments are configured to receive at least a portion of a sampler.

2. The analytical device of claim 1, wherein the first surface energy gradient coating comprises species X1-J1-M1 and species X2-J2-M2 wherein X1, X2, M1, and M2 represent separate functional groups where M1 and M2 have different surface energies and J1 and J2 represents spacer moieties, and the molar concentration of the species X2-J2-M2 increases relative to the molar concentration of the species X1-J1-M1 in the gradient surface energy coating from the first sealed compartment or second compartment to the reaction region.

3. The analytical device of claim 1, wherein the extraction solvent comprises a phosphate buffer solution with a pH of 7 to 9.

4. The analytical device of claim 1, wherein the detection region comprises at least a portion of a lateral flow strip.

5. The analytical device of claim 1, wherein the reaction region comprises at least a portion of a lateral flow strip.

6. The analytical device of claim 1, further comprising a second fluid passage connecting the reaction region to the detection region wherein the second fluid passage comprises a second surface energy gradient coating.

7. The analytical device of claim 6, wherein the second surface energy gradient coating comprises species X1-J1-M1 and species X2-J2-M2 wherein X1, X2, M1, and M2 represent separate functional groups where M1 and M2 have different surface energies and J1 and J2 represents spacer moieties, and the molar concentration of the species X2-J2-M2 increases relative to the molar concentration of the species X1-J1-M1 in the gradient surface energy coating from the reaction region to the detection region.

8. The analytical device of claim 6, wherein the device comprises a fourth compartment comprising a liquid reagent and a third fluid passage connecting the fourth compartment to the detection region or reaction region wherein the third fluid passage comprises a third surface energy gradient coating.

9. The analytical device of claim 1, wherein the device comprises a fourth compartment comprising a liquid reagent and a second fluid passage connecting the fourth compartment to the detection region or reaction region.

10. The analytical device of claim 9, wherein the second fluid passage comprises a second surface energy gradient coating.

11. The analytical device of claim 10, wherein the second surface energy gradient coating comprises species X1-J1-M1 and species X2-J2-M2 wherein X1, X2, M1, and M2 represent separate functional groups where M1 and M2 have different surface energies and J1 and J2 represents spacer moieties, and the molar concentration of the species X2-J2-M2 increases relative to the molar concentration of the species X1-J1-M1 in the gradient surface energy coating from the fourth compartment to the reaction or detection region.

12. The analytical device of claim 1, wherein the sampler comprises a first portion and a second portion wherein the first portion is configured to collect a sample and the second portion comprises sealing means to seal against the opening of the second compartment.

13. The analytical device of claim 12, wherein the first and second compartments together are sized to enclose the first portion of the sampler.

14. The analytical device of claim 12, wherein the third compartment is sized to enclose the first portion of the sampler.

15. The analytical device of claim 12, wherein the sealing means of the second portion comprises an axial or radial seal.

16. The analytical device of claim 12, wherein the sealing means of the second portion is selected from the group consisting of an O-ring, a threaded cap, a press-fit seal, a gasket, and a cap closure.

17. The analytical device of claim 12, wherein the sample comprises a food sample.

18. The analytical device of claim 12, wherein the sample comprises a soil or water sample.

19. The analytical device of claim 12, wherein the sample comprises a biological sample.

20. The analytical device of claim 19, wherein the biological sample comprises a human biological sample.

* * * * *